(12) United States Patent
Coppens et al.

(10) Patent No.: US 11,071,606 B2
(45) Date of Patent: Jul. 27, 2021

(54) ADJUSTABLE IMMOBILIZER APPARATUS AND METHOD FOR IMMOBILIZING A PATIENT

(71) Applicant: Qfix Systems, LLC, Avondale, PA (US)

(72) Inventors: Daniel D. Coppens, Avondale, PA (US); David M. Rabeno, Avondale, PA (US); Stephen J. Reiser, Glen Mills, PA (US)

(73) Assignee: Qfix Systems, LLC, Avondale, PA (US)

( * ) Notice: Subject to any disclaimer, the term of this patent is extended or adjusted under 35 U.S.C. 154(b) by 0 days.

(21) Appl. No.: 16/223,848

(22) Filed: Dec. 18, 2018

(65) Prior Publication Data
US 2019/0117330 A1    Apr. 25, 2019

Related U.S. Application Data

(63) Continuation of application No. 14/913,760, filed as application No. PCT/US2015/014090 on Feb. 2, 2015.
(Continued)

(51) Int. Cl.
*A61G 15/00*     (2006.01)
*A61B 90/18*     (2016.01)
(Continued)

(52) U.S. Cl.
CPC .............. *A61B 90/18* (2016.02); *A61B 90/14* (2016.02); *A61F 5/05841* (2013.01);
(Continued)

(58) Field of Classification Search
CPC ......... A61B 90/18; A61B 90/14; A61B 90/10; A61B 90/00; A61B 6/0421; A61B 6/04;
(Continued)

(56) References Cited

U.S. PATENT DOCUMENTS

| | | | |
|---|---|---|---|
| 3,417,438 A | 12/1968 | Schuplin | |
| 4,592,352 A * | 6/1986 | Patil ....................... | A61B 90/11 5/637 |

(Continued)

FOREIGN PATENT DOCUMENTS

| | | |
|---|---|---|
| CN | 1684636 A | 10/2005 |
| DE | 3340482 A1 | 5/1985 |

(Continued)

OTHER PUBLICATIONS

Medtec Calatog, Advanced Patient Positioning and Fixation, Estro 2004, 12 pages.
(Continued)

*Primary Examiner* — Victoria J Hicks
(74) *Attorney, Agent, or Firm* — RatnerPrestia

(57) ABSTRACT

Systems for immobilizing a patient are disclosed. The system includes at least one preform formed from a low melting temperature thermoplastic, the preform being configured to be formed to the anatomy of the patient, at least one frame coupled to the at least one preform, and at least one support configured to support the anatomy of the patient. The system also includes at least one lock mechanism coupled to at least one of the frame and the support and configured to couple the at least one frame to the at least one support, and at least one adjuster mechanism coupled to at least one of the at least one frame and the at least one support and configured to selectively adjust a distance between the at least one frame and the at least one support while the at least one frame is coupled to the at least one support.

27 Claims, 26 Drawing Sheets

Related U.S. Application Data

(60) Provisional application No. 62/102,358, filed on Jan. 12, 2015, provisional application No. 61/941,542, filed on Feb. 19, 2014.

(51) Int. Cl.

| | |
|---|---|
| *A61F 5/37* | (2006.01) |
| *A61F 5/058* | (2006.01) |
| *A61B 90/14* | (2016.01) |
| *A61B 6/04* | (2006.01) |
| *A61N 5/10* | (2006.01) |

(52) U.S. Cl.
 CPC ........ *A61F 5/05858* (2013.01); *A61F 5/3707* (2013.01); *A61B 6/0421* (2013.01); *A61N 2005/1096* (2013.01); *A61N 2005/1097* (2013.01)

(58) Field of Classification Search
 CPC .............. A61B 6/0428; A61B 8/40; A61B 2018/00321; A61F 5/05841; A61F 5/05; A61F 5/05858; A61F 5/0585; A61F 5/05883; A61F 5/37; A61F 5/3707; A61F 5/0104; A61F 5/058; A61F 5/05891; A61F 2009/0035; A61N 2005/1097
 USPC ........................................................ 128/845
 See application file for complete search history.

(56) References Cited

U.S. PATENT DOCUMENTS

| | | | |
|---|---|---|---|
| 5,370,117 A | 12/1994 | McLaurin | |
| 5,531,229 A | 7/1996 | Dean et al. | |
| 5,566,681 A | 10/1996 | Manwaring et al. | |
| 5,702,406 A | 12/1997 | Vilsmeier et al. | |
| 5,730,745 A | 3/1998 | Schulte et al. | |
| 5,775,337 A | 7/1998 | Hauger et al. | |
| 6,282,739 B1 * | 9/2001 | Livingston ............... | A61N 5/10 5/640 |
| 6,376,846 B2 | 4/2002 | Livingston | |
| 6,698,045 B1 | 3/2004 | Coppens et al. | |
| 6,749,384 B1 | 6/2004 | Ellis | |
| 6,865,411 B2 | 3/2005 | Erbel et al. | |
| 7,063,461 B2 | 6/2006 | Coppens et al. | |
| 7,120,954 B2 | 10/2006 | Traut et al. | |
| 7,213,597 B2 | 5/2007 | Huttner | |
| 7,290,548 B2 | 11/2007 | Ungemach et al. | |
| 7,461,657 B2 | 12/2008 | Woodburn | |
| 8,613,716 B2 | 12/2013 | Summit et al. | |
| 8,874,251 B2 | 10/2014 | Thornton | |
| 2002/0038659 A1 * | 4/2002 | Al-Kassim ............ | A61F 5/3707 128/845 |
| 2002/0073487 A1 | 6/2002 | Phillips et al. | |
| 2002/0120986 A1 | 9/2002 | Erbel et al. | |
| 2007/0156141 A1 | 7/2007 | Cuypers et al. | |
| 2008/0078410 A1 | 4/2008 | De Mooy et al. | |
| 2012/0186588 A1 | 7/2012 | Wilson et al. | |
| 2014/0182603 A1 | 7/2014 | Coppens et al. | |
| 2015/0047652 A1 | 2/2015 | De Mooij | |

FOREIGN PATENT DOCUMENTS

| | | |
|---|---|---|
| EP | 1095640 A1 | 5/2001 |
| EP | 1537831 A1 | 6/2005 |
| EP | 1900326 A1 | 3/2008 |
| NL | 1039586 C | 11/2013 |
| WO | 2011049548 A1 | 4/2011 |
| WO | 2013167688 A1 | 11/2013 |
| WO | 2014193938 A1 | 12/2014 |
| WO | 2015021377 A2 | 2/2015 |
| WO | 2015126605 A1 | 8/2015 |

OTHER PUBLICATIONS

Encompass Head Fixation System User Manual, Med-Tech, Nov. 6, 2003, 16 pages.
Description of the McLaurin Arch, dated Aug. 30, 1998.
Med Tech McLaurin Marketing Collateral, Stabilization arches: bite block and nasal surfaces, 1 page.
McLaurin Fast Fit, "Fractionated Accelerator-Based Stereotactic Teletheraphy", Proceedings of the American Society of Therapeutic Radiology and Oncology, Nov. 4-8, 19991, 1 page.
Aquaplast Corp RT Literature, AccuFix Cantilever Board with Shoulder Depression for IMRT Treatment, 2003, 12 pages.
AquaPlast Z-Fix Systems Product Catalog, email version 2008, 84 pages.
McKernan et al., "Surface laser scanning to routinely produce casts for patient immobilization during radiotherapy", Australian Radiology, 2007, vol. 51, pp. 150-153.
Med Tec, Great Lakes TEC Gazette, 2003, 2 pages.
Tech Times, Spring 2003, vol. 8, Issue 1, 12 pages.
Encompass SRS Immobilization System brochure, 2003, 4 pages.
Med Tech Estro 2004 brochure, "Advanced Patient Positioning and Fixation", 13 pages.
Med Tech ASTRO 2004 Brochure, 2004, Advanced Patient Positionng and Fixation, 13 pages.
Tech Times Brochure, vol. 7, Issue 2, 16 pages, Fall 2002.
Tech Times, vol. 8, Issue 1, Spring 2003 Brochure, 12 pages.
Med Tec Encompass Head Fixation System User Manual, Nov. 6, 2003, 16 pages.
Tec Times TYPE-S Updates, 2003, 1 page.
Tech Times, vol. 7, Issue 2, Fall 2002, 2 pages.
MedTech ESTRO 2004, Advanced Patient Positioning and Fixation, 2 pages.
Medtec ASTRO 2004, Advanced Patient Positioning and Fixation, 2 pages.
Astro 2004 Brochure, Type S Variable Axis Baseplate, 4 pages.
International Preliminary Report on Patentability for International Application No. PCT/US2015/014090, dated Aug. 23, 2016.
International Search Report for International Application No. PCT/US2015/014090, dated Apr. 17, 2015, 24 pages.
Chinese Office Action for Chinese Application No. 201580002000.8, dated Mar. 16, 2018, including English translation, 30 pages.
Chinese Office Action for Chinese Application No. 201580002000.8, dated Dec. 10, 2018, 21 pages.
Non Final Office Action for U.S. Appl. No. 14/913,760, dated Dec. 12, 2019, 49 pages.
Extended European Search Report for European Application No. 20 208 169.1, dated Mar. 11, 2021, 8 pages.
Extended European Search Report for European Application No. 20 208 163.4, dated Mar. 11, 2021, 6 pages.
Final Office Action for U.S. Appl. No. 14/913,780, dated Oct. 28, 2020, 31 pages.
Indian Examination Report for Indian Application No. 201617027303, dated Mar. 16, 2020, with translation, 7 pages.
European Communication Pursuant to Article 94(3) for European Application No. 15706968.3, dated Jun. 5, 2020, 5 pages.
Chinese Office Action for Chinese Application No. 201580002000.8, dated Jul. 1, 2019 with partial translation, 18 pages.
Non Final Office Action for U.S. Appl. No. 14/913,760, dated Jun. 8, 2021, 25 pages.

\* cited by examiner

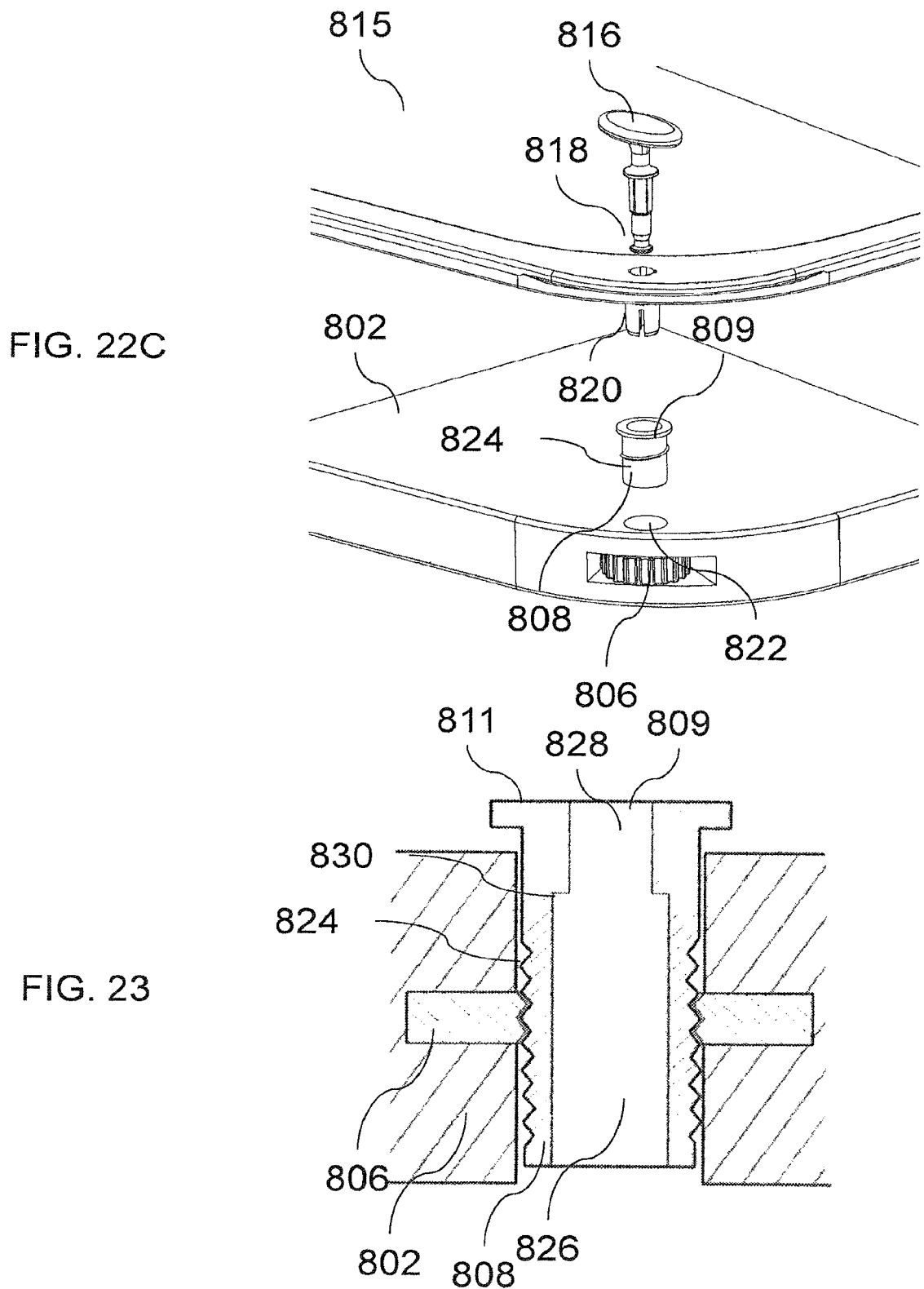

ADJUSTABLE IMMOBILIZER APPARATUS AND METHOD FOR IMMOBILIZING A PATIENT

CROSS-REFERENCE TO RELATED APPLICATIONS

This application is a continuation of U.S. patent application Ser. No. 14/913,760, filed Feb. 23, 2016, which is a U.S. National Phase Application of PCT Application No. PCT/US2015/014090, filed Feb. 2, 2015, which claims the benefit of U.S. Provisional Application No. 62/102,358, filed on Jan. 12, 2015, and U.S. Provisional Application No. 61/941,542, filed on Feb. 19, 2014, the contents of each of these applications being incorporated by reference in their entireties herein for all purposes.

BACKGROUND OF THE INVENTION

There is a growing need for improved devices that can immobilize patients or patient anatomies. For example, thermoplastic sheets are known and used as patient immobilizers in radiation therapy to reduce or prevent movement of patient anatomies during therapy. Such sheets are heated to become formable, formed over a part of a patient's anatomy, and then cooled to harden, thereby immobilizing the patient or patient's anatomy for the treatment therapy.

Patient immobilization is particularly important when performing stereotactic radiosurgery. In this procedure a high dose of radiation is delivered to the patient over one or a small number of treatments. A high degree of patient immobilization is required.

Despite developments that have been made in connection with such devices, there remains a need for improved patient immobilizers as well as improved methods and processes for immobilizing patients in terms of at least one of cost control, enhanced performance, and ease of use.

SUMMARY OF THE INVENTION

Aspects of the present invention are directed to apparatus, systems, and methods for adjustably immobilizing a patient.

In accordance with one aspect of the present invention, a system for immobilizing an anatomy of a patient is disclosed. The system includes at least one preform formed from a low melting temperature thermoplastic, the preform being configured to be formed to the anatomy of the patient, at least one frame coupled to the at least one preform, and at least one support configured to support the anatomy of the patient. The system also includes at least one lock mechanism coupled to at least one of the at least one frame and the at least one support and configured to couple the at least one frame to the at least one support, and at least one adjuster mechanism coupled to at least one of the at least one frame and the at least one support and configured to selectively adjust a distance between the at least one frame and the at least one support while the at least one frame is coupled to the at least one support.

Further aspects of the invention include a system for immobilizing an anatomy of a patient. The system includes an immobilization element contoured to receive the anatomy of the patient, and a support configured to support the anatomy of the patient. The system also includes a lock mechanism coupled to at least one of the support and the immobilization element and configured to affix the support with respect to the immobilization element, and an adjuster mechanism coupled to at least one of the support and the immobilization element, the adjuster mechanism being configured to selectively adjust a distance between the support and the immobilization element while the immobilization element is coupled to the support.

Additional aspects of the invention are directed to an apparatus for immobilizing an anatomy of a patient. The apparatus includes a preform formed from a low melting temperature thermoplastic, the preform being configured to be formed to the anatomy of the patient, and a frame coupled to the preform and adapted to be coupled to a support configured to support the anatomy of the patient. The apparatus also includes a lock mechanism coupled to the frame and configured to couple the frame to the support, and an adjuster mechanism coupled to the frame and configured to selectively adjust a distance between the frame and the support while the frame is coupled to the support.

Other aspects of the invention include a method of immobilizing an anatomy of a patient for treatment. The method includes forming an immobilization element corresponding to the anatomy of the patient by heating a preform to a forming temperature, positioning the heated preform with respect to the anatomy of the patient and a support supporting the anatomy of the patient, and activating a lock mechanism to lock the preform with respect to the support and immobilize the anatomy of the patient with respect to the support with the immobilization element. The method also includes adjusting, while the anatomy of the patient is in place in the immobilization element, a distance between the immobilization element and the support by selectively adjusting at least one adjuster mechanism coupled to at least one of the preform, the support, and the immobilization element.

Even further aspects of the invention include a system for immobilizing an anatomy of a patient with respect to a patient anatomy support. The system includes an immobilization device, means for locking the immobilization device with respect to the patient anatomy support, and means for adjusting a distance between the immobilization device and the patient anatomy support while the immobilization device is coupled to the patient anatomy support.

BRIEF DESCRIPTION OF THE DRAWINGS

The invention is best understood from the following detailed description when read in connection with the accompanying drawings, with like elements having the same reference numerals. When a plurality of similar elements is present, a single reference numeral may be assigned to the plurality of similar elements with a small letter designation referring to specific elements. Included in the drawings are the following figures:

FIGS. 22A, 22B, and 22C depict adjustment of an adjustment mechanism according to aspects of the invention;

FIG. 23 is a cross-sectional view of an adjustment mechanism in accordance with aspects of the invention;

DETAILED DESCRIPTION OF THE INVENTION

Figure 1A:
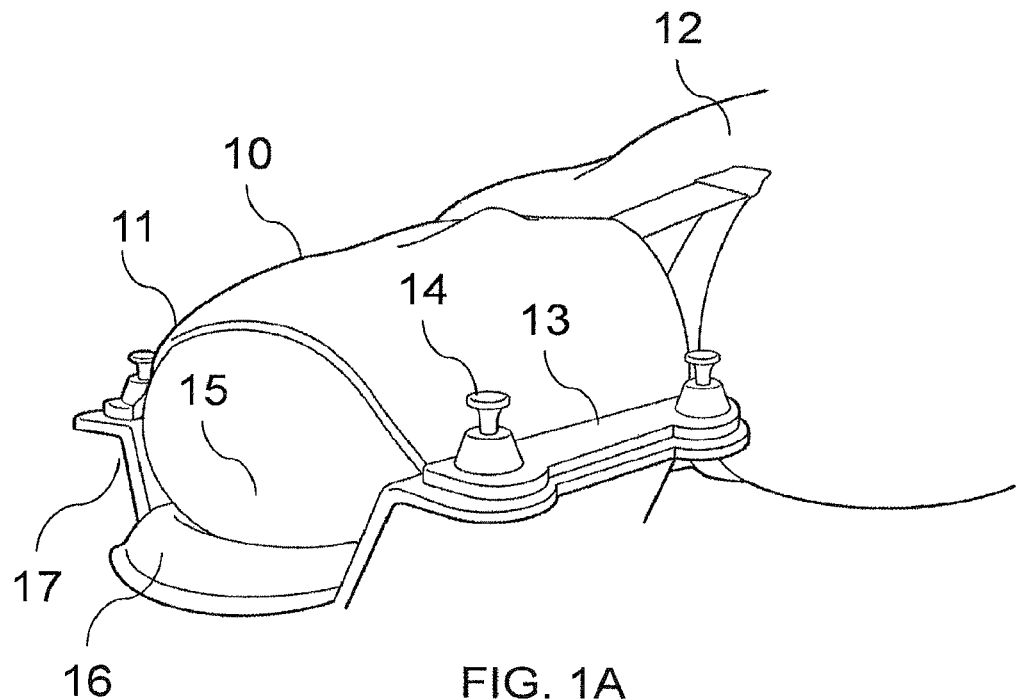
FIGS. 1A and 1B are diagrams illustrating an exemplary layout for an immobilization device for use during radiotherapy, neurosurgery or for general cranial immobilization in accordance with aspects of the present invention. These diagrams demonstrate an embodiment that is particularly well suited to neurosurgery as the apex of the head remains uncovered and accessible.

Aspects of the present invention relate generally to apparatus and methods for immobilizing patients. The apparatus and methods disclosed herein desirably provide adjustable, non-invasive patient immobilization. As used herein, non-invasive patient immobilization refers to immobilization without the need for components that physically attach to the patient (e.g., bone screws).

In order to sate for changes in a patient's anatomy over time, patient thermoplastic immobilization solutions for Stereotactic RadioSurgery (SRS) and radiation therapy optionally include a series of loose and/or separate "shim" components. These shims can be added or subtracted to either tighten the immobilization system or to loosen it. This is required in order to obtain a high degree of immobilization while maintaining an acceptable level of patient comfort. Patients may gain or lose volume (e.g. fat, water) from the time of simulation to the time of treatment or subsequent fractions. Such shimming requirements can result in a large number of components and associated locking clips to accommodate varied shim thickness. Shims can run from 0 mm to 4 mm in 1 mm increments. Also, such shimming requires removing the immobilization device from the anatomy of the patient and cannot be performed with the immobilization device in place.

Shimming can be cumbersome and adds a significant amount of time to the patient setup process. Systems that lack a shimming capability, however, cannot adequately adapt to patient geometry to provide sufficient immobilization in certain applications. Accordingly, preferred embodiments of this invention can eliminate the use of separate shim components while providing adjustment for improved immobilization. In addition, embodiments of this invention permit adjustment without removing the system from the patient.

Embodiments of the present invention are particularly advantageous for use during stereotactic radiosurgery and radiation therapy, but may also be utilized for cancer treatment, radiosurgery, occupational therapy, splinting, plastic surgery, surgery, invasive neurosurgery, etc. Those of skill in the art will understand other treatments for which the disclosed apparatus and methods may be utilized. During stereotactic radiosurgery, a high dose of radiation is delivered precisely to an area of the patient (such as a region of the patient's head). When a patient is referred for stereotactic radiosurgery they will first undergo a process known as simulation. The purpose of this process is to acquire an image (typically a DICOM data set) for planning and treatment with the patient immobilized in the same devices and position that will be used during treatment and to perform imaging of the patient using techniques such as computed tomography (CT), magnetic resonance (MR), positron emission tomography (PET), or a hybrid imaging technique such as PET/CT or PET/MR. Depending on the case, clinical center, and techniques being used this simulation step may occur on the same day of treatment or may occur up to a week or more prior to treatment. In cases where an invasive immobilization frame is used, simulation and treatment typically occur on the same day in order to minimize stress to the patient and opportunities for complications. Accordingly, a thermoplastic mask may be used to immobilize the patient in accordance with aspects of the present invention.

This low melting temperature thermoplastic mask, also referred to herein as a preform, will then be used to immobilize the patient each time the patient returns for treatment. There are instances in which it is desirable to adjust the anterior/posterior position of this mask with respect to the patient. This can occur for a number of reasons including shrinkage of the thermoplastic mask and weight loss or gain of the patient. Additionally, the preform may accommodate the use of a bite block to immobilize the patient's upper palette. Examples of bite blocks are described in PCT Application No. PCT/US14/39764, entitled "HEAD AND JAW IMMOBILIZATION DEVICE", the contents of which are incorporated by reference herein. Aspects of the present invention provide for this adjustment through, in one embodiment, adjustable locking mechanisms (e.g., locking pins). While any number of locking pins can be used, in a preferred embodiment six locking pins are used for each thermoplastic mask. The locking pins can either be permanently or removably attached to the frame of the mask.

Figure 1B:
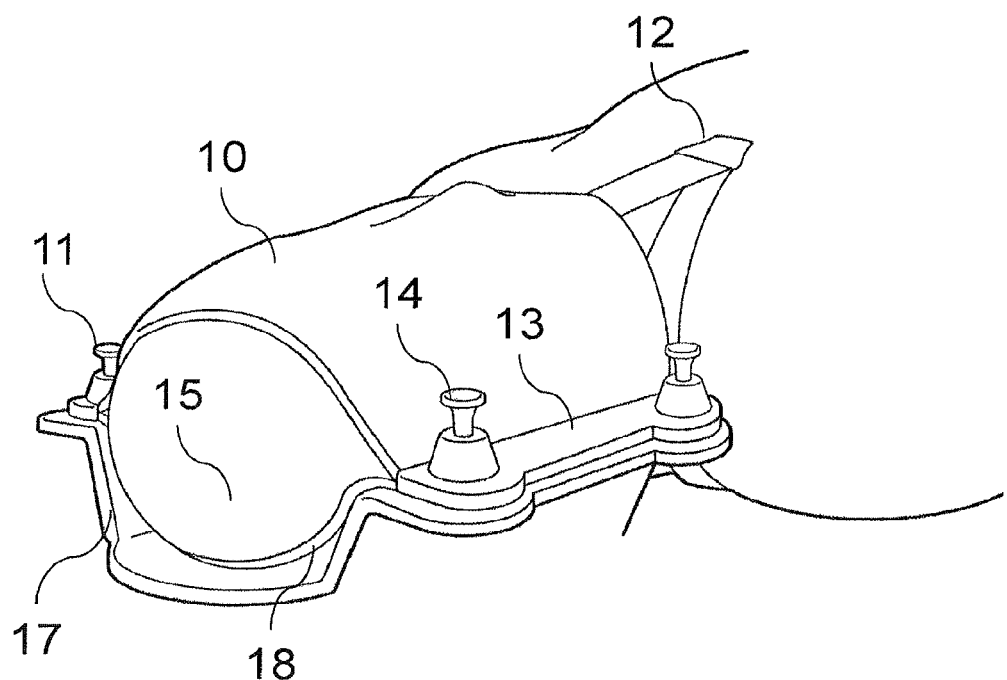
Figure 2:
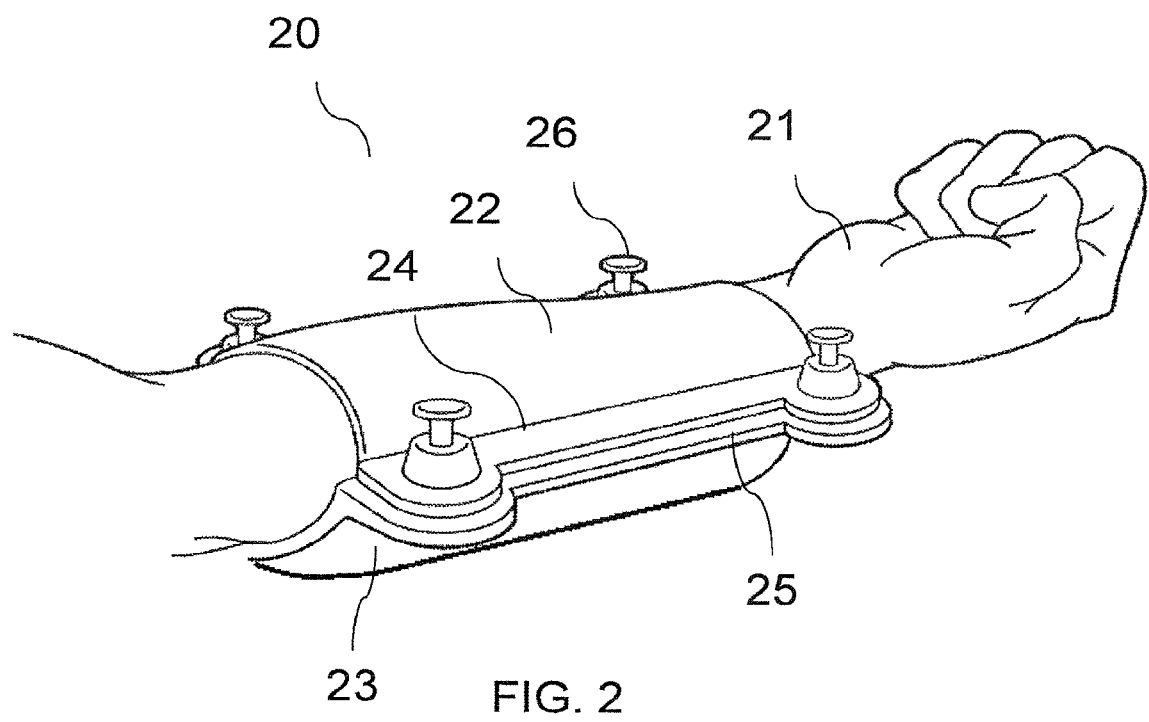
FIG. 2 is a diagram illustrating an exemplary layout for an immobilization device for use in immobilizing a patient's anatomy in accordance with aspects of the present invention.

While the present embodiments are described herein with respect to stereotactic radiosurgery, it will be understood that the invention is not so limited. Aspects of the present invention may be used in any application where patient immobilization is required. Other suitable applications include immobilizing a patient for neurosurgery (as shown in FIGS. 1A and 1B), immobilizing injured or broken bones of a patient (as shown in FIG. 2), or immobilizing a patient during medical scans or imaging, such as magnetic resonance imaging.

In general, exemplary patient immobilization devices in accordance with aspects of the present invention include a shape corresponding to a portion of the patient's anatomy formed from a low melting temperature thermoplastic. An immobilization device can optionally include a frame component, an integral frame portion, or can be provided without any frame. In other words, the frame is optionally a portion of the immobilization device or a preform, or both. The immobilization device may be a preform, constructed from a low-melting temperature thermoplastic, configured to be formed to an anatomy of a patient. The immobilization device may also be formed from a rigid, semi-rigid, or non-rigid material, contoured to an anatomy of a patient.

According to one embodiment, a frame is coupled to the preform to stabilize and support the preform. A lock mechanism (e.g., a locking mechanism, a lock, etc.) is either permanently or removably coupled to the frame. The lock mechanism can be attached to the frame in the unlocked state and in the locked state. The lock is configured to couple the frame to a patient support. For example, the frame may be locked to the support, attached to the support, in place on the support in an unlocked state. An adjuster mechanism (e.g., an adjustment mechanism, and adjuster, etc.) is coupled to at least one of the frame and the patient support. The adjuster mechanism can be attached to the frame when the lock mechanism is in the unlocked state and in the locked state. The adjuster is configured to provide selective adjustment of the distance (e.g., the vertical height) between the frame and the patient support.

In accordance with other aspects of the invention, exemplary patient immobilization devices include a cushion retaining device which is used in conjunction with a formable patient cushion. The cushion retaining device provides support for the cushion and hence increases the rigidity and repeatability of the placement of the cushion. This cushion retaining device may be used in conjunction with the preform and frame described previously to provide superior patient immobilization. Additional details of aspects of the present invention are provided below with reference to the drawings.

Figure 3A:
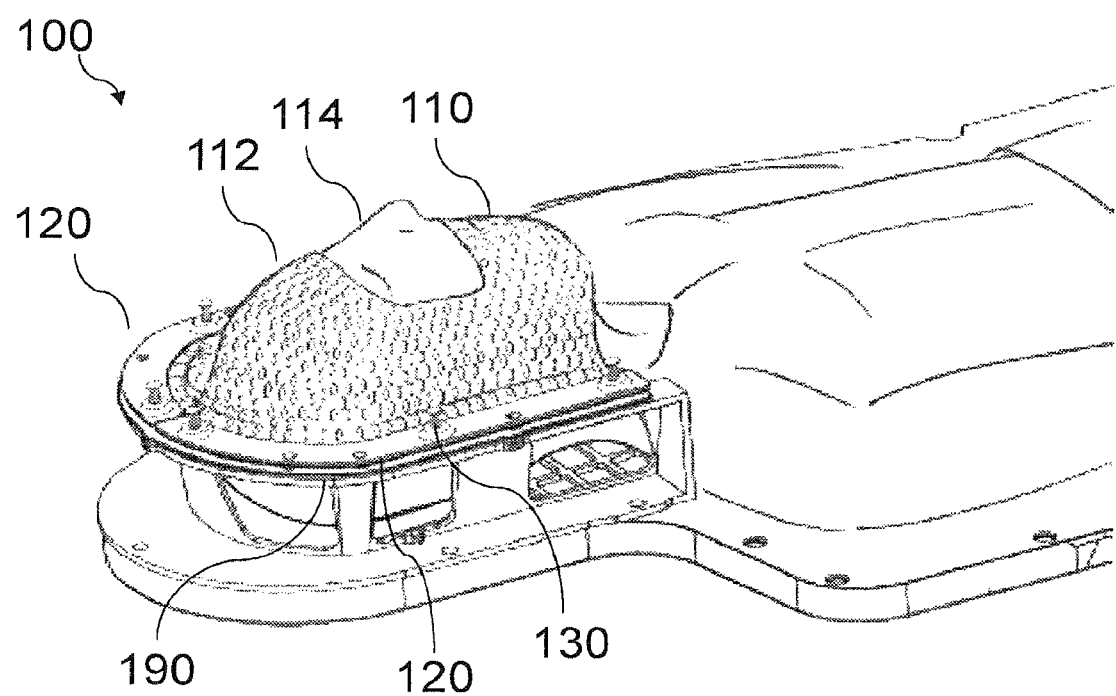
FIGS. 3A, 3B and 3C are diagrams illustrating an exemplary apparatus configured for immobilizing a patient in accordance with aspects of the present invention.
Figure 3B:
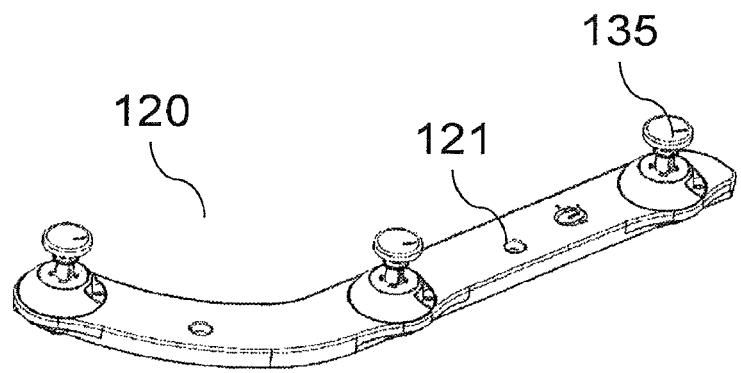
Figure 3C:
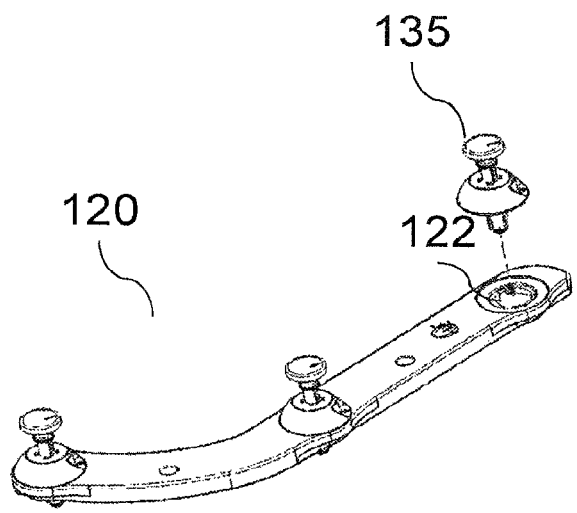

FIGS. 3A 3B, and 3C illustrate an exemplary apparatus 100 configured for immobilizing a patient in accordance with an aspect of the present invention. Apparatus 100 may be usable to immobilize a patient during a medical procedure involving the patient's head, such as stereotactic radiosurgery. As a general overview, apparatus 100 includes a preform 110, a frame 120, and at least one lock 130. Additional details of apparatus 100 are described below.

Preform 110 is formed over an anatomy of the patient. The positioning of preform 110 may be selected based on the procedure to be performed on the patient. In an exemplary embodiment, preform 110 is formed to the patient's head, as illustrated in FIG. 3A. In this embodiment, preform 110 may include a plurality of cutouts 114 in order to facilitate comfort of the patient, as well as allow the user to breath/see through preform 110. Preform 110 may also a plurality of perforations 112 in areas that do not affect the ability of preform 110 to immobilize the patient.

Preform 110 may be formed from a low melting temperature thermoplastic. Suitable thermoplastics include, for example, polycaprolactone (PCL). To create the shape of the patient's anatomy, preform 110 is first heated to a forming temperature (e.g., a temperature above its melting temperature), which causes the preform to enter a state in which it is pliable. Preform 110 may be heated using a number of methods including, for example, a hot water bath or an oven. While the preform is in this heated state, it is pressed against or around the patient's anatomy (e.g., the patient's head) and allowed to cool. Once cooled, the thermoplastic retains the shape of the patient's anatomy and becomes rigid, thereby preventing or resisting movement of the patient. The thermoplastic of preform 110 may be of any thickness, the thickness being chosen based on the level of rigidity required for the application or procedure. For stereotactic radiosurgery applications, preform 110 preferably has a thickness of at least about 3 mm. Filler materials may be optionally added to the thermoplastic in order to increase the stiffness of the material.

Additional details regarding the features of preform 110, or any other aspects of the present invention, may be found in U.S. Patent Application Publication No. 2014/0182603 A1, and in Patent Cooperation Treaty Application No. PCT/US2014/039764, the contents of each of which are incorporated herein by reference.

Frame 120 is coupled to preform 110. Frame 120 provides support for preform 110 during and following the process of forming preform 110 to the shape of the patient's anatomy. As shown in FIG. 3A, more than one frame 120 may be used for a respective preform 110.

Like preform 110, frame 120 is shaped to correspond to the portion of the patient's anatomy to be immobilized by apparatus 100. Frame 120 may be constructed of any material, including a thermoplastic material, so long as the melting temperature of the frame material is higher than that of the preform. Thus, frame 120 will retain its rigid shape and support preform 110 when preform 110 is deformed to correspond to the shape and contour of the patient's anatomy.

Together, preform 110 and frame(s) 120 form a patient restraint that can be attached to a patient support 190 in order to immobilize the patient. While one patient restraint is illustrated in FIG. 3A, it will be understood that apparatus 100 may employ multiple patient restraints to immobilize the patient. For example, apparatus 100 may include an anterior patient restraint and a posterior patient restraint sized to mate or attach to one another. The frame 120 is attached to the patient support 190 via locks 130 positioned around the frame 110.

Referring to FIGS. 3B and 3C, the frame 120 includes a plurality of openings 121. Openings 121 are provided so that frame 120 can be aligned properly to other structures, such as patient support 190. The patient support 190 may include protrusions adapted to fit through the openings 121 such that the frame can be positioned on the patient support 190. The frame 120 may also include a series of ports 122 adapted to receive a lock and adjuster 135 (reference numeral 135 as used herein refers to the lock and adjuster in combination in accordance with some embodiments). In addition to being secured to preform 110, frame 120 may also be placed on and secured to a support structure 190 in order to immobilize the patient relative to the support structure 190, as shown in FIG. 3A. In an exemplary embodiment, frame 120 is secured to preform 110 and/or support structure 190 using one or more locks 130, as will be described below. Alternatively, frame 120 may be secured to preform 110 or support structure 190 using bolts, screws, pins, or other conventional securements, which will be known to one of ordinary skill in the art from the description herein.

The lock 130 is movably positioned within an opening 122 of frame 120. The lock 130 may also be co-located with an adjuster so as to form the lock and adjuster 135, permitting adjustment of the distance between frame 120 and support structure 190, and to fix frame 120 in a position relative to support structure 190. In one example, the adjuster (e.g., adjustment mechanism, variable shim, adjustable shim, etc.) may be rotated in order to adjust the distance of frame 120. Lock 130 may also secure frame 120 to preform 110.

By providing an adjuster coupled to at least one of the frame 120 or the patient support 190, the number of parts to be handled by the user is drastically reduced. This leads to improvements in efficiency for the cancer treatment center. This adjuster can take many forms including but not limited to a stepped slider, a wedge, a wheel, and a cam. By rotating or sliding these forms of the adjuster, the position of frame with respect to the support surface is changed. The adjuster may be permanently or removably attached to the frame of the mask or the support surface.

The adjuster mechanism can have a surface positioned for movement relative to a frame. For example, a rotatable member may be provided such that one aspect of the member is a ramped surface. If this ramped surface is positioned between the immobilization member and the surface it is placed, a rotation of this member will change the position of the immobilization member. This may similarly be performed by a ramped or stepped sliding member.

In an exemplary embodiment, lock 130 is inseparable from frame 120, such that lock 130 cannot be removed from frame 120 without disassembly of one or both components. Alternatively, lock 130 may be removably attached to frame 130, e.g., by pulling upward with sufficient force on lock 130. As with the other components of apparatus 100, lock 130 is preferably constructed from materials that are compatible with the procedure to be performed on the patient, such as polymers.

Figure 4A:
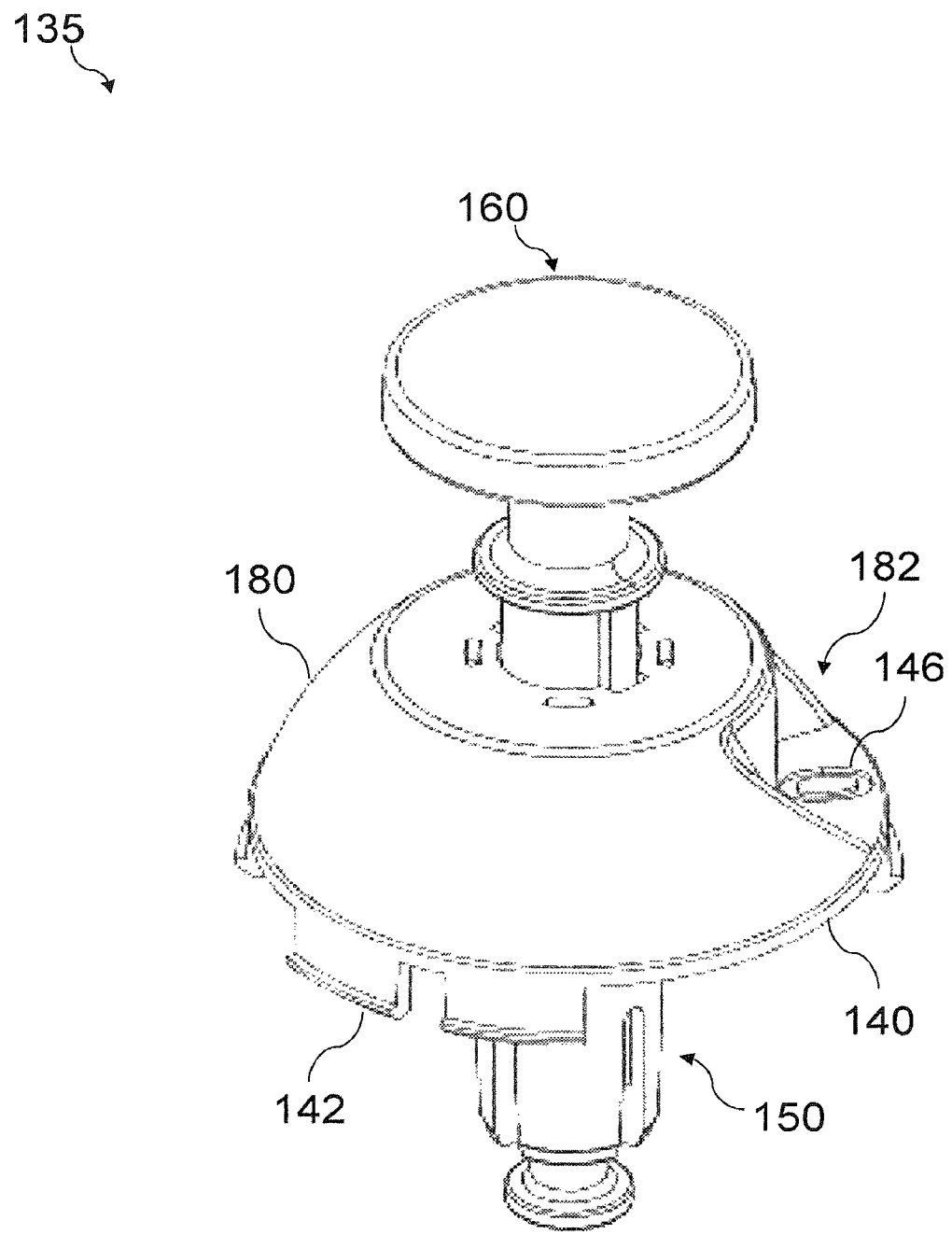
FIGS. 4A, 4B, 4C, 4D, and 4E are diagrams illustrating an exemplary lock and adjuster mechanism in accordance with aspects of the invention.
Figure 4B:
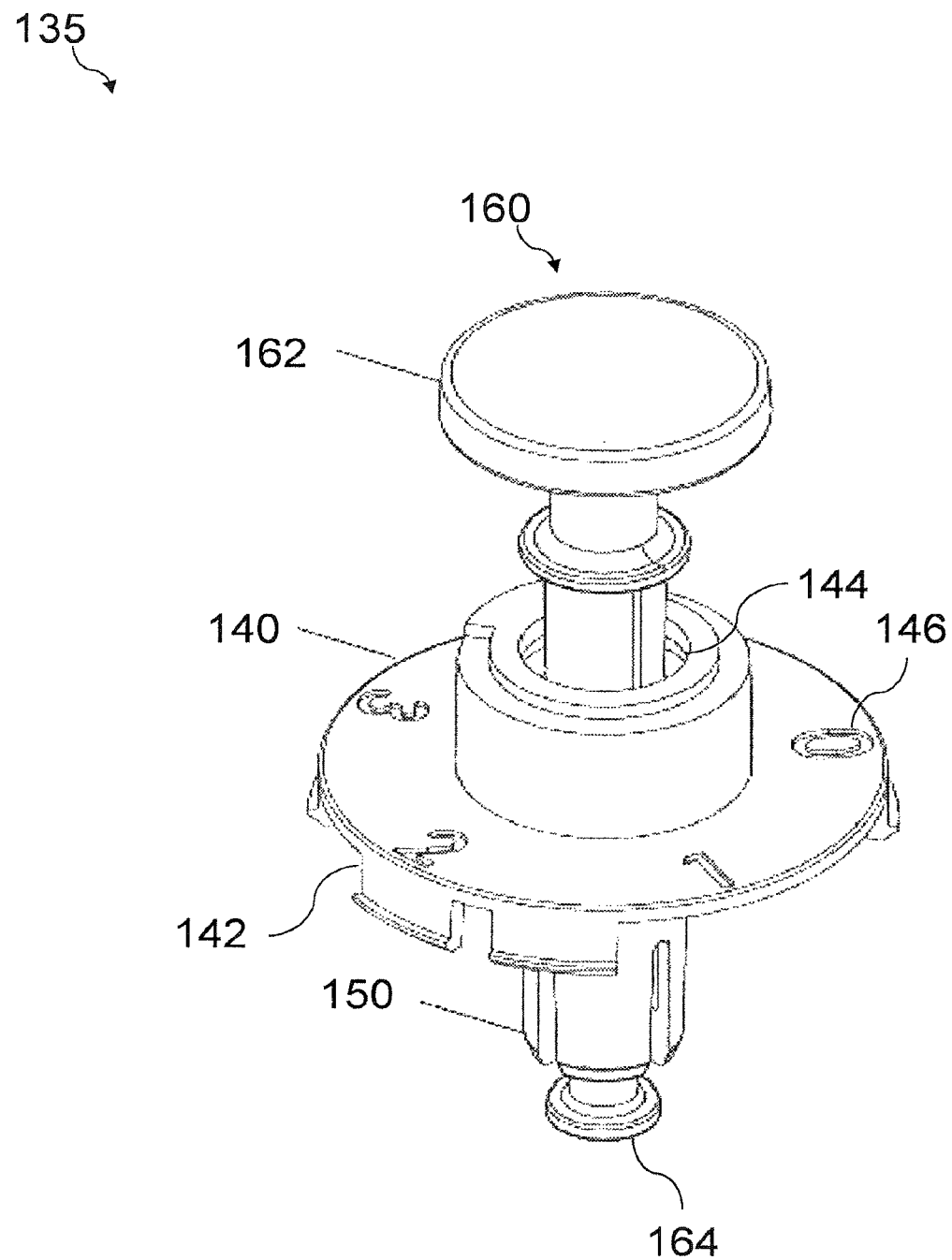
Figure 4C:
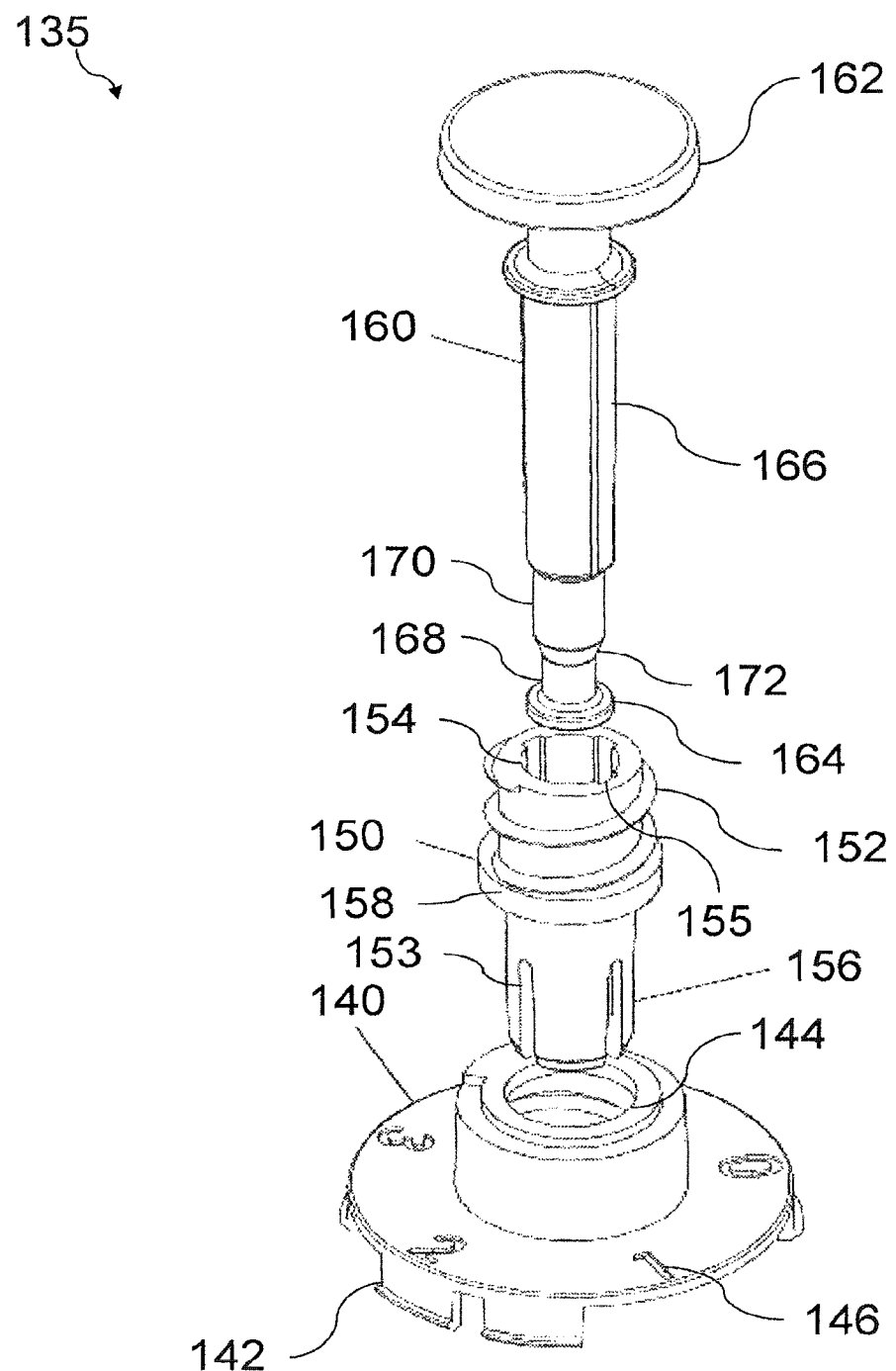

FIGS. 4A-4C illustrate an example of a co-located lock and adjuster 135 in accordance with aspects of the present invention. As a general overview, the co-located lock and adjuster 135 includes a shaft 150, and a plunger 160, and a casing 140. Additional details of the co-located lock and adjuster 135 are provided below.

Casing 140 provides a base for the co-located lock and adjuster 135. Casing 140 may attach the lock and adjuster 135 directly to frame 120. As shown in FIGS. 4A and 4B, casing 140 may include a plurality of protrusions 142 sized to mate or engage with a port 122 of frame 120 in order to secure casing 140 (and consequently co-located lock and adjuster 135) to frame 120. Protrusions 142 may create a removable or fixed attachment of casing 140 to frame 120. Alternatively, casing 140 may be integrally formed as part of frame 120.

Casing 140 further includes a through-hole 144 for accommodating shaft 150 and plunger 160. The interior of through-hole 144 includes threading (not shown) sized and pitched to mate with corresponding threading on shaft 150. In an exemplary embodiment, casing 140 includes a plurality of numeric indicators 146 on an upper surface thereon, the purpose of which will be described in detail below.

Shaft 150 is sized to be received within the threaded through-hole 144 of casing 140. The features of shaft 150 are shown in the exploded view provided in FIG. 4C. However, shaft 150 is normally contained within casing 140, and is not removable therefrom. Shaft 150 includes threading 152 sized and pitched to mate with the threading on the interior of casing 140. Accordingly, rotation of the bonnet 180 causes rotation of the shaft 150 within through-hole 144, which vertically displaces the shaft 150 relative to casing 140 based on the pitch of the engaging threads.

Shaft 150 includes a through-hole 154 for accommodating plunger 160, as shown in FIG. 4C. Through-hole 154 includes one or more keying features 155 on the wall thereof. Keying features 155 mate with corresponding features on plunger 160, thereby coupling rotation of plunger 160 to shaft 150, as will be described below.

The lock mechanism can have a surface positioned to resist separation of the frame from the support. The lock mechanism can have at least one extension positioned to create an interference lock when the lock mechanism is in the locked state, the at least one extension providing the surface positioned to resist the separation of the frame from the support. In the embodiment illustrated in FIG. 4C, shaft 150 further includes one or more extensions 156 separated by gaps 153 at a lower end thereof. Extensions 156 protrude from a lower end of casing 140 when shaft 150 is received within casing 140, as shown in FIGS. 4A and 4B. Shaft 150 may also include a flange 158. Like extensions 156, flange 158 is positioned outside of a lower end of casing 140 when shaft 150 is received within casing 140. Flange 158 may be sized to bear against a surface of an adjacent structure (such as support structure 190).

Plunger 160 includes a plurality of segments having variable diameters. In an exemplary embodiment, plunger 160 includes a first segment 168 having a first diameter and a second segment 170 having a second diameter. A tapered portion 172 connects the first and second segments 168 and 170. Plunger 160 is sized to be received within the through-hole 154 of shaft 150. Plunger 160 includes a knob 162 at an upper end thereof to enable a user of apparatus 100 to easily press or turn locking pin 130. Plunger 160 further includes a flange 164 at a lower end thereof. Plunger 160 includes one or more keying features 166, as shown in FIG. 4C, which are sized to mate with keying features 155 on shaft 150.

The locking mechanism (e.g., the lock) is provided by the interaction between the flange 164, extensions 156, first segment 168, second segment 170, keying features 166, gaps 153 and tapered portion 172. The adjustment mechanism (e.g., the adjuster) is provided by the interaction between the plunger 160, the knob 162, the keying features 166, the threading 152, the threaded through-hole 144, and the keying features 155.

In the first (or unlocked) state, plunger 160 is in an undepressed position. In this state, segment 168 having the smaller diameter is positioned radially inward from extensions 156 (or radially inward from the projections formed on the inner walls of extensions 156, if included). Segment 168 is sized so that it does not bear against extensions 156, and as a result, extensions 156 remain in a normal, unforced position (parallel to the axis of plunger 160, as shown in FIGS. 4A and 4B). In this unforced position, extensions 156 do not contact the inner walls of the mating hole on support structure 190, and shaft 150 is free to move relative to support structure 190 (e.g., by rotation of plunger 160).

In the second (or locked) state, plunger 160 is in a depressed position. The lock mechanism can have at least one extension positioned to create an interference lock when the plunger is in the locked state. During depression of plunger 160, tapered portion 172 is pressed against extensions 156 until segment 170 having the larger diameter is positioned radially inward from extensions 156 (or radially inward from the projections formed on the inner walls of extensions 156, if included). Segment 170 is sized so that it bears against extensions 156, and as a result, extensions 156 are forced radially outward. In this forced position, extensions 156 bear against or lock with the inner walls of the mating hole on support structure 190, and shaft 150 is locked in place relative to support structure 190. It is contemplated that the locking mechanisms may be integrated into the support structure rather than the frame of the preform.

The operation of the lock in one example is provided as followed. Extensions 156 are positioned within a mating hole on a structure to which a frame 120 is to be attached, e.g., in support structure 190. Depressing the plunger 160 moves the flange 164 at the end of the second segment 170 downward. The flange 164, second segment 170, tapered portion 172 and first segment 168 extend downward pass the extensions 156. The larger diameter of the first segment 168 forces the extensions 156 radially outward. The bottom portion of the keying features 166 may then extend into the gaps 153 between the extensions 156. The contact between the first segment 168, the keying features 166, the extensions 156 and the gaps 153 provide sufficient force to lock the lock and adjuster 135 with respect to a frame or patient support. To release the lock, the plunger 160 may be returned to its original position, which removes the keying features 166 and the first segment 168 from contact with the extensions 156. The lock optionally may locate the mask with respect to the support surface or this function may be performed by another feature such as a pin or boss.

The adjustment mechanism (e.g., adjuster) operates as followed according to one example of the invention. The plunger and the shaft can rotate together relative to the frame. The keying features 166 are received by keying features 155, which causes the shaft 150 to rotate upon rotation of the plunger 160, via the interaction between the threading 152 and the treaded through-hole 144. Rotation of the plunger 160 (e.g., via the knob 162) adjusts the position of the flange 158 with respect to the other components. Advantageously, the adjustment may be performed with the co-located lock and adjuster 135 are either in the locked state or in the unlocked state.

In operation, flange 158 contacts a surface of support structure 190 surrounding the mating hole in which extensions 156 are positioned. Accordingly, vertical movement of shaft 150 relative to casing 140 results in movement of the adjacent surface of support structure 190 relative to casing 140. In other words, rotating shaft 150 within casing 140 adjusts the vertical distance or spacing of casing 140 (and thereby frame 120) relative to support structure 190 due to the contact between flange 158 and the surface of support structure 190.

Figure 4D:
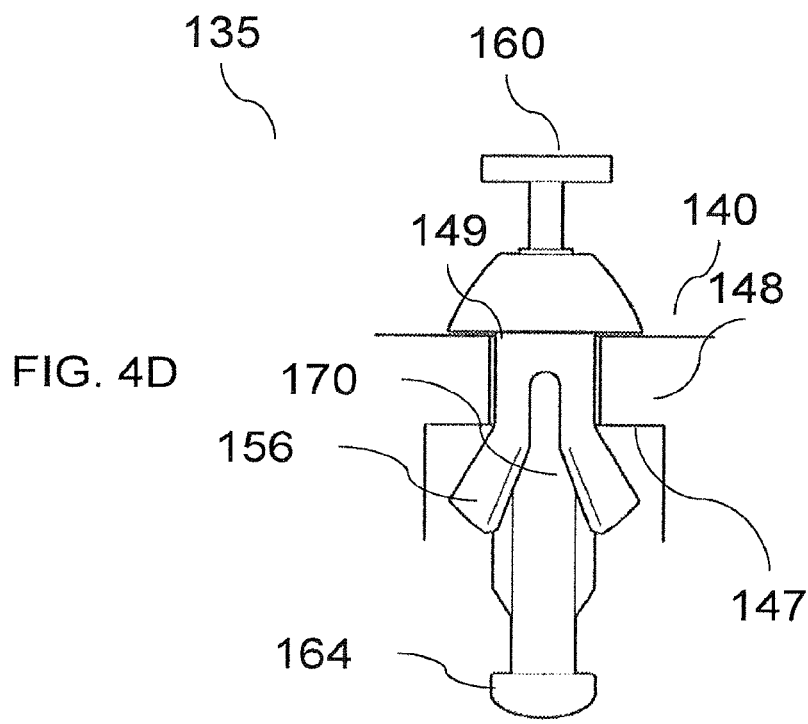

FIG. 4D is a cross sectional diagram of the co-located mechanism 135 in the locked position. Depressing the plunger 160 extends it through an opening 149 in the structure 148 (the structure 148 being, for example, a frame, a support, etc.). The first section 170 of diameter larger than the second section pushes the extensions 156 radially outward such that they extend partially over the edge 147 of the opening 149. The extension of the extensions 156 creates an interference lock between the elements being locked. The lock mechanism can include an interference lock configured to create interference between the lock and at least one of the frame and the support. In one aspect of the invention, the adjuster mechanism advantageously cannot be adjusted when the lock is in the locked position, such that the distance between the support and the frame cannot be changed. This may be preferred in some applications to prevent inadvertent adjustment of the distance between the support and the frame. For example, it may be beneficial to avoid inadvertent loosening of the immobilization element from the anatomy of the patient during treatment. In an embodiment, the radially outward extension of the extensions 156 of the mechanism 135 while in a locked position prevent rotation of the plunger 160 such that the adjustment mechanism may not be activated.

Figure 4E:
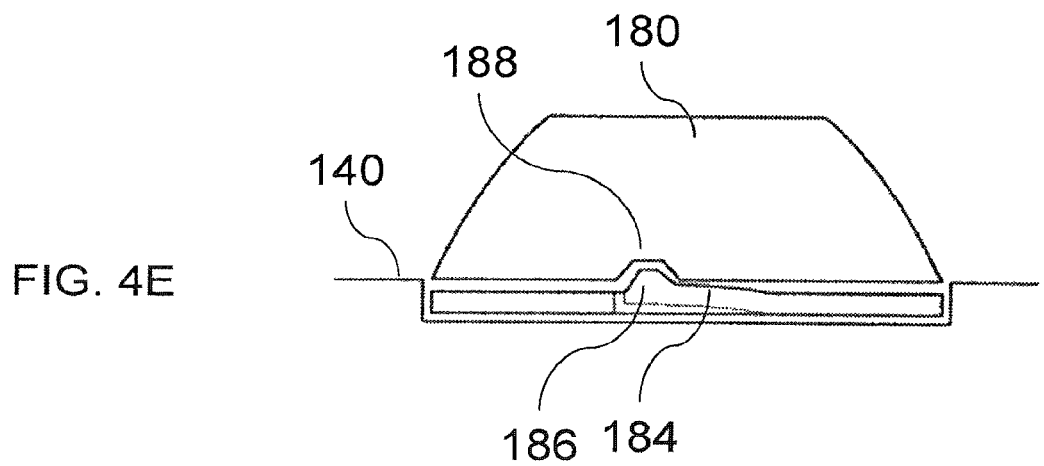

As described above, the mechanism 135 may also include an indexing mechanism as shown in FIG. 4E. The bonnet 180 has formed in it grooves 188 that are configured to receive a protrusion 186 formed at the end of a flange 184 (e.g., a spring). Rotation of the bonnet 180 may push the protrusion 186 out of the groove 188 by depressing the flange 184 downward. When the bonnet 180 is rotated to another discrete position as is formed by a groove 188, the spring force of the flange 184 pushes the protrusion 186 into the groove 188, which may cause an audible indication (e.g., a click noise), that the bonnet 180 has been rotated to a next discrete position. Other indexing mechanisms may be utilized as will be understood by those of skill in the art, such as a cam, step, etc.

Figure 5A:
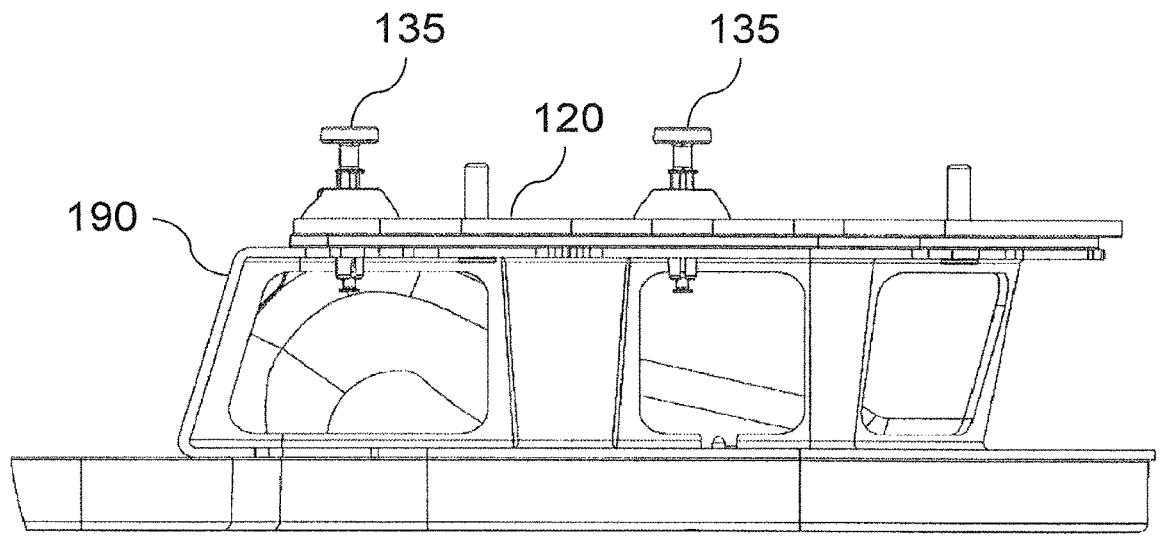
FIGS. 5A and 5B are diagrams illustrating an exemplary operation for adjusting a distance of the frame relative to a support for the system in accordance with aspects of the invention.
Figure 5B:
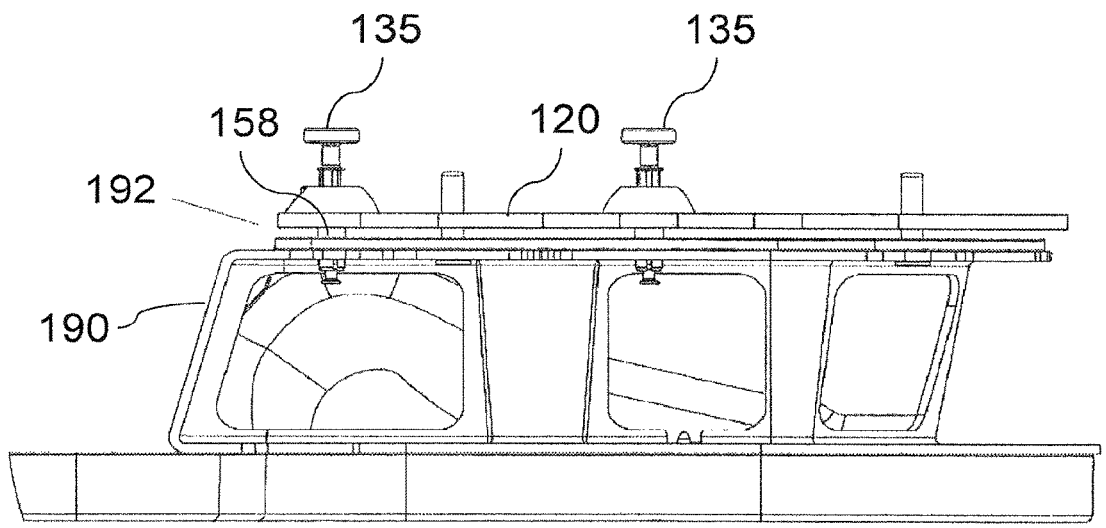

A change in the distance of frame 120 relative to support structure 190 according to the above operation is illustrated in FIGS. 5A and 5B. As shown in FIG. 5A, frame 120 is coupled to the support structure 190. In this state, the adjuster 135 is adjusted to rotate the shaft 150 to be at a vertically upper position within casing 140 (i.e. an "unscrewed position"). In contrast, as shown in FIG. 5B, a space 192 is created between frame 120 and support structure 190. In this state, the adjuster 135 is adjusted to rotate the shaft 150 to be at a vertically lower position within casing 140 (e.g., a "screwed in position"), causing flange 158 to push against support structure 190 and force frame 120 upward and away from support structure 190.

By the above operation, the precise distance of frame 120 (and thus apparatus 100) from support structure 190 may be adjusted and controlled. This distance may be adjusted in predetermined increments (e.g., 1 mm increments) using detents within casing 140, or may be adjusted continuously over a predetermined range. In order to accommodate the degree of adjustments that may be required for a number of different patients or medical procedures, it may be desirable that casing 140 and shaft 150 enable total adjustment (or vertical distance) of at least 4 mm.

Generally, one advantage conferred by embodiments of this invention is the ability to adjust the distance between an immobilization device and a patient support while the two are coupled to one another. Such coupling may include a locked arrangement, a partially locked arrangement (for example in a system with multiple locks or adjusters when only some but not all of the locks are engaged), an unlocked arrangement, or an arrangement in which the immobilization device is not removed or separated from the patient support. Accordingly, a coupling between the immobilization device and the patient support contemplates any of these possible arrangements.

Apparatus 100 is not limited to the above components, but may include additional or alternative components as would be understood by one of ordinary skill in the art from the description herein.

An indicator can be positioned to provide a visual indication of the distance maintained between a frame and a support at a location at which an adjuster mechanism is coupled to the frame. For one example, a bonnet 180 may be provided for visual indications to a user regarding the spacing of frame 120 (e.g., position of the locking mechanism) from support structure 190. As explained above, casing 140 may include indicators 146 on an upper surface thereof. In this embodiment, the bonnet 180 may include a window 182 for selectively revealing the indicators to a user of the locking pin 130. Bonnet 180 is coupled to plunger 160 in order to be rotated. As shown in FIG. 4A, bonnet 180 includes a window 182 to selectively reveal one of the indicators 146 on casing 140 based on the rotated position of bonnet 180.

It is preferred but not required that the bonnet 180 (and thereby the shaft 150) rotate to discrete locations around the arc. These discrete locations correspond to predetermined positions that are preferred for treatment. By rotating to discrete locations it can be assured that a snug, repeatably fitting mask is achieved each time. The position may be adjusted with the mask already in place on the patient or may be adjusted prior to placing the mask on the patient. An indexing mechanism, such as a spring or cam, may be provided to cause the rotation of the plunger 160 to be stopped (or triggered) at discrete locations. In an example, the indexing mechanism provides a clicking sound to indicate that a discrete location has been reached by the adjuster.

Figure 6:
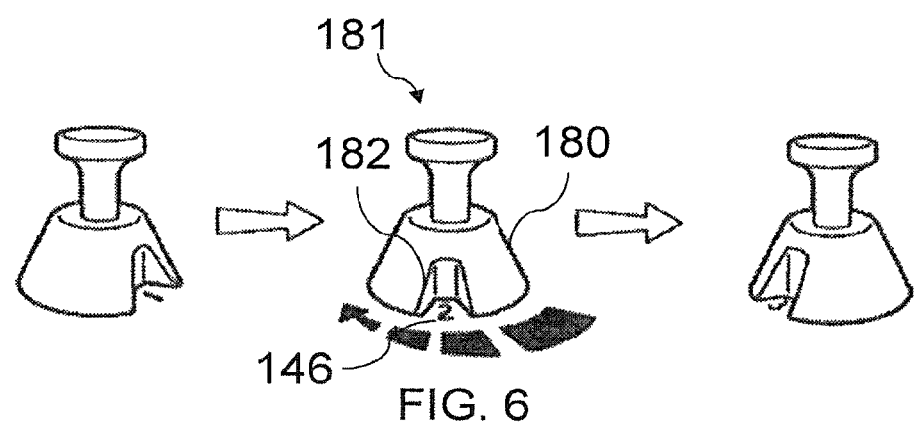
FIGS. 6 and 7 are diagrams showing exemplary discrete and continuous adjustments, respectively, according to aspects of the invention.

Advantageously, the adjuster may provide for both discrete and continuous adjustment. For example, the indexing mechanism may be configured to index rotation at discrete locations, but the adjuster may be rotated and stopped at positions between or outside the indexed discrete locations. For discrete operation, casing 140 and/or shaft 150 may include detents to allow adjustment of the distance in predetermined increments (e.g., 1 mm). In this embodiment, each detent may be associated with a particular indicator 146 on casing 140. Accordingly, as the lock and adjuster 135 is adjusted through each increment, window 182 of bonnet 180 is configured to reveal the corresponding indicator 146 on casing 140. This feature desirably provides a visual indication to a user of apparatus 100 of the spacing created or maintained at that location. An exemplary operation of an adjuster 181 with bonnet 180 through a plurality of numeric increments is shown in FIG. 6.

Figure 7:
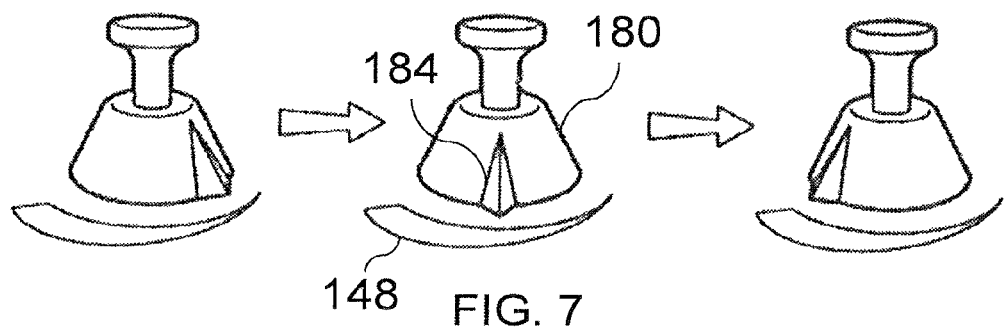

For continuous operation, casing 140 may include a single, continuously varying indicator 148, as shown in FIG. 7, as opposed to discrete numeric indicators 146. In this embodiment, bonnet 180 may include an arrow or other projection 184 for visually indicating to the user the degree of spacing using the continuously varying indicator 148.

For another example, apparatus 100 may include separate adjusting and locking components. While the co-located lock and adjuster 135 is described herein as a single component capable of performing both adjustment and fixing functions, it will be understood that those functions can be separated. An exemplary embodiment of a frame 120 including separate locking and adjusting components is illustrated in FIGS. 8 and 9.

Figure 8:
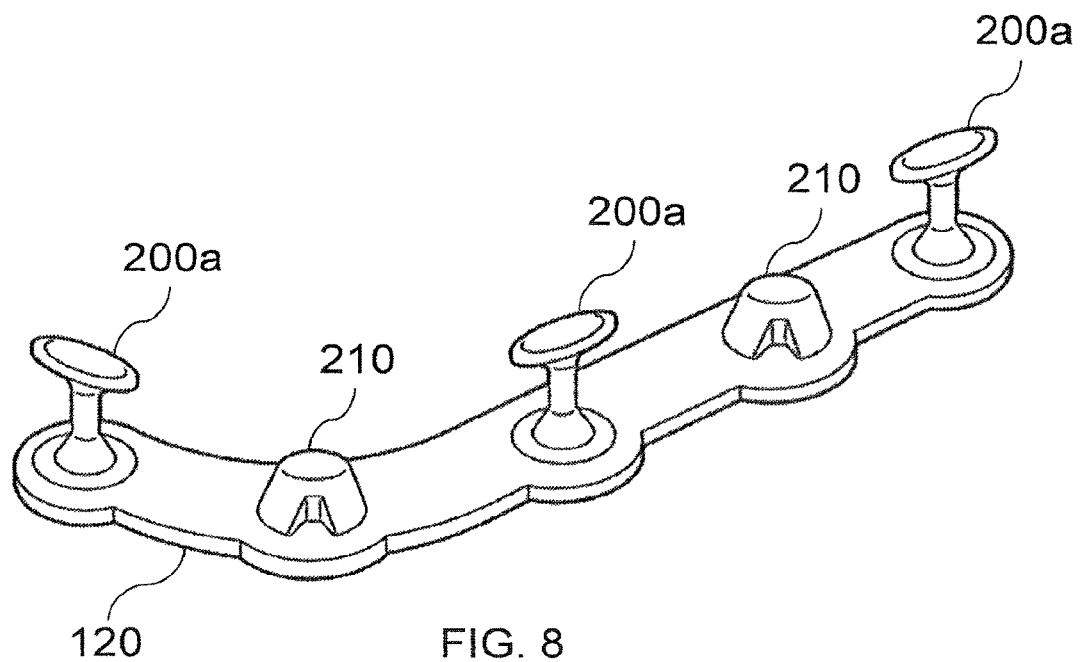
FIGS. 8 and 9 are diagrams showing alternative locking and adjustment mechanisms in accordance with aspects of the present invention.

As shown in FIG. 8, frame 120 may include a first set of locks 200a including the plunger/shaft extension interaction of locking mechanism of lock and adjuster 135, and a second set of components 210 (e.g., adjusters) integrated separately from the locks 200a in the frame 120. Locking mechanisms 200a function to lock frame 120 in place by forcing extensions to bear against or lock with a mating hole on an adjacent structure, as described above. Adjusters 210 function to adjust the spacing between frame 120 and an adjacent structure by allowing a user to turn the exposed knob in discrete or continuous increments.

Figure 9:
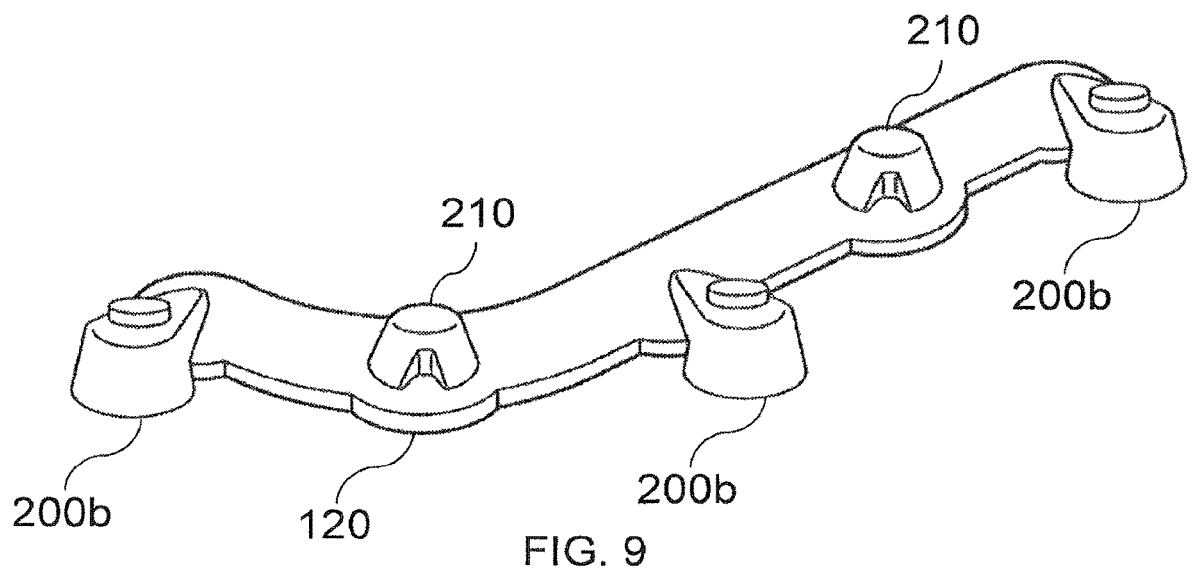

While locking mechanisms 200a are illustrated in FIG. 8 as including a locking plunger, it will be understood that other locking mechanisms may be employed, such as swivel locking mechanisms 200b, as shown in FIG. 9. Advantageously, the locking mechanisms 200a and the adjusters 210 are separately integrated, such that locks 200 are coupled to another structure, such as a patient support. Alternatively, the locks 200 may be integrated into the frame while the adjusters 210 may be integrated into another structure, such as a patient support. Other suitable mechanisms for locking frame 120 in a position relative to a support structure will be known to one of ordinary skill in the art from the description herein. For example, the locking mechanisms can be positioned on the frames, support structures, etc. and may be integrated separately from the variable shims, together with the variable shims, or a combination thereof. Furthermore, the adjusters may be integrated in the frames, support structures, interposed elements, etc. and may be integrated separately from the locks, together with the locks, or a combination thereof.

In an embodiment of the invention the locks are attached to the frame of the thermoplastic immobilization device. In this embodiment a split frame is shown in which the left and right side of the frame are not connected other than with the thermoplastic preform. This split frame type allows a mask to be formed while minimizing the amount of stretch to the preform.

In an embodiment, a support structure is provided on which the frame of the thermoplastic mask rests when immobilizing a patient. This support structure provides the mating holes for the lock to engage. By raising this support structure anterior with respect to the patient support surface it is possible to increase the resistance of the mask to movement. This is accomplished because raising this support structure reduces the length of the sidewall of the mask. It also reduces the amount of stretch of the mask required to form the mask around the patient's anatomy. The height of the support structure can be any height chosen to optimize the rigidity of the mask while maintaining clearance for desired treatment beam paths. Preferably, this height is approximately 8 cm above the patient support surface. The support structure also provides locating pins which position the immobilization member with respect to the support structure. These are in addition to the locking pins. These locating pins provide a tightly tolerance locational accuracy which ensures the repeatability of placement of the immobilization members.

Figure 10:
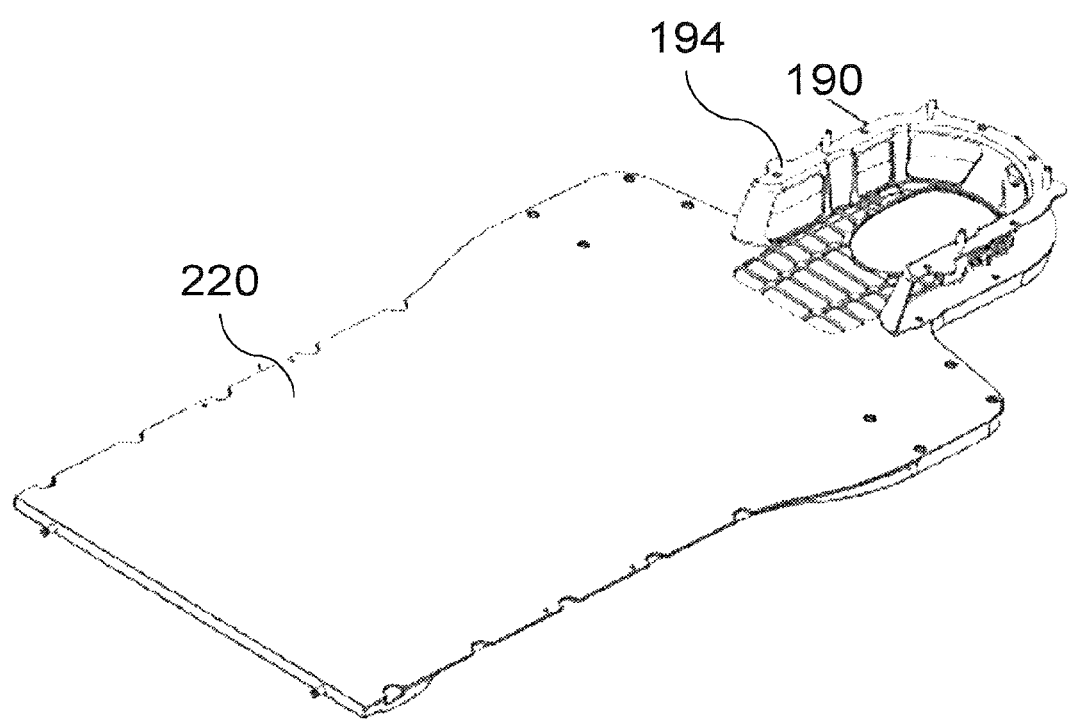
FIG. 10 is a diagram illustrating an exemplary support in accordance with aspects of the invention.

For still another example, apparatus 100 may include a patient support 220. An exemplary patient support 220 is illustrated in FIG. 10. Patient support surface 220 is a large, flat surface on which the patient can be positioned during the medical procedure. Suitable patient supports include beds, tables, gurneys, or other well-known surfaces on which a seated or supine patient can be positioned. Support structure 190 may be integrally formed with support surface 220, or may be a separate structure 190 that is placed on and movably positioned with respect to support surface 220. When support structure 190 is separate from patient support surface 220, it may be desirable that support structure 190 be removably attached to surface 220 to enable consistent, repeatable positioning of support structure 190. Suitable components for removably attaching support structure 190 to surface 220 will be known to one of ordinary skill in the art from the description herein.

Support structure 190 is positioned on patient support 220 such that a top surface 194 thereof is positioned anterior to patient support surface 220. In an exemplary embodiment, the top surface 194 of support structure 190 is spaced a predetermined distance (e.g., approximately 10 cm) from patient support surface 220.

Figure 14:
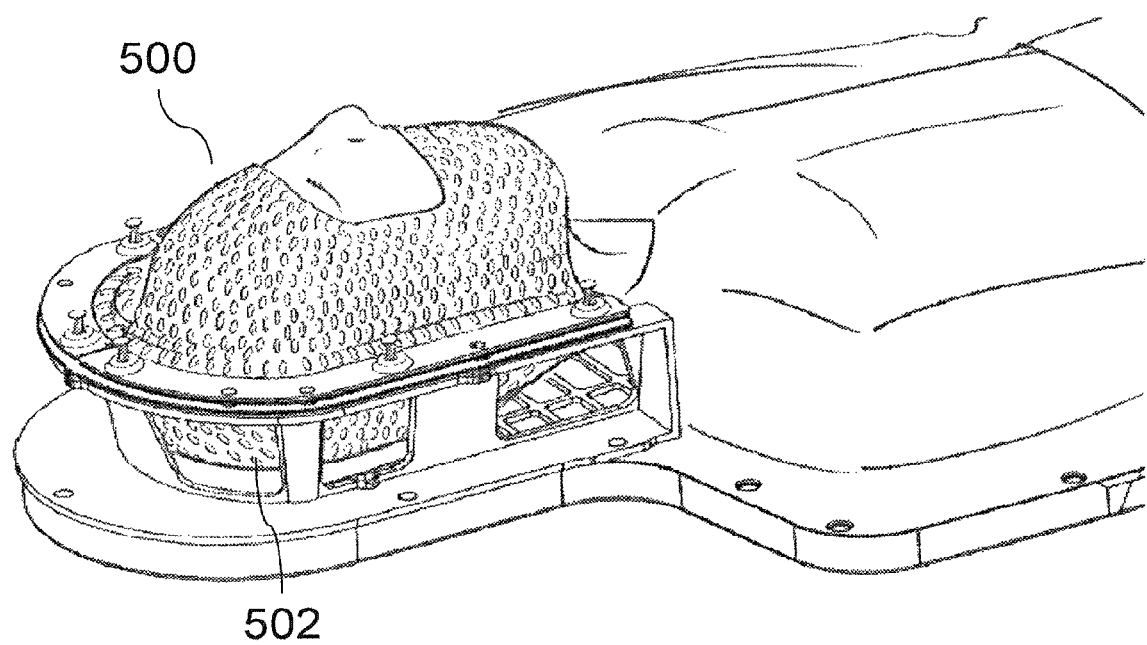
FIG. 14 is a diagram of a support and immobilization device according to aspects of the invention.

In addition to the support surface and immobilizations element, additional elements may be interposed between the support surface and the frame of the immobilization element. These can include items such as additional preforms, cushions, cushion retaining devices or any alternative elements understood by one of ordinary skill in the art from the description herein. Cushions and cushion retaining devices are shown as examples in FIGS. 11A, 11B and 19. An interposed posterior mask preform is shown as examples in FIG. 15 in its unformed condition. Item 18 in FIG. 1B and item 502 in FIG. 14 show examples of interposed posterior masks in their formed state. Adjustment mechanisms may be optionally coupled to one or more interposed elements.

Figure 11A:
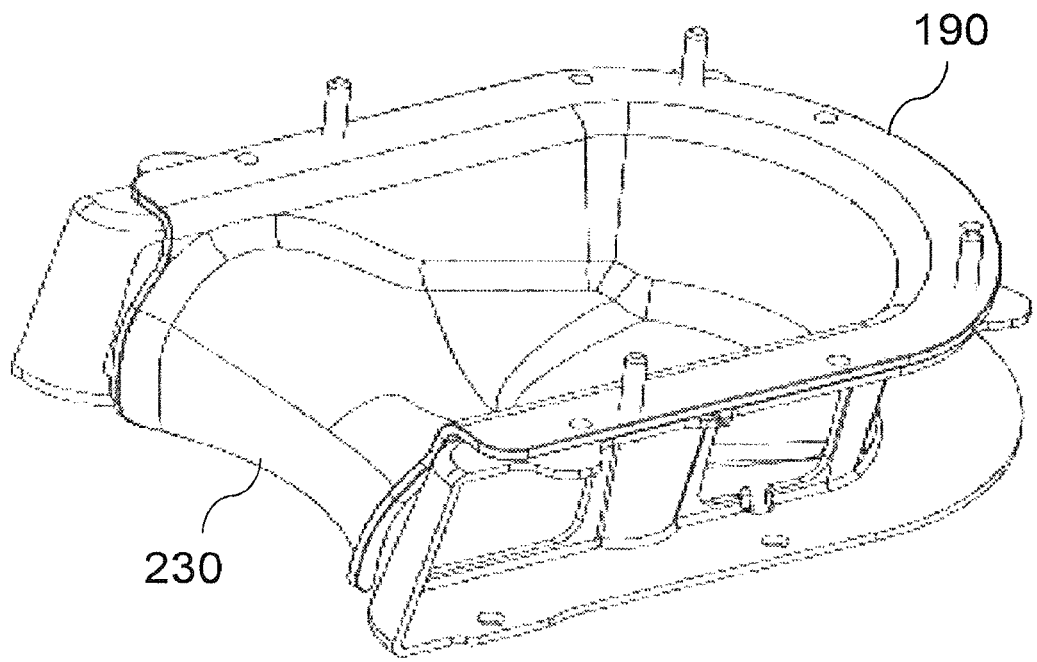
FIGS. 11A and 11B are diagrams illustrating an exemplary cushion retaining device.
Figure 11B:
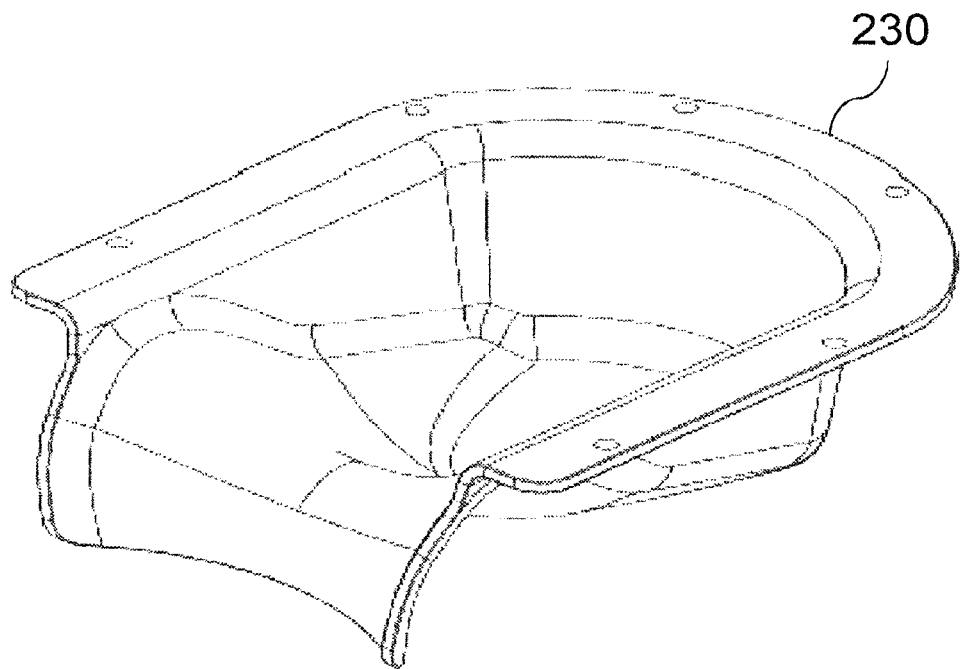

In addition to support structure 190, apparatus 100 may include a cushion retaining device 230 for retaining a formable cushion. An exemplary cushion retaining device 230 is illustrated in FIGS. 11A and 11B. The formable cushion is used to support the portion of the user's anatomy in a stable, immobile position. Additional details regarding formable cushions for use with the present invention, or any other aspects of the present invention, may be found in Patent Cooperation Treaty Application No. PCT/US2014/050335, the contents of which are incorporated herein by reference.

Figure 19:
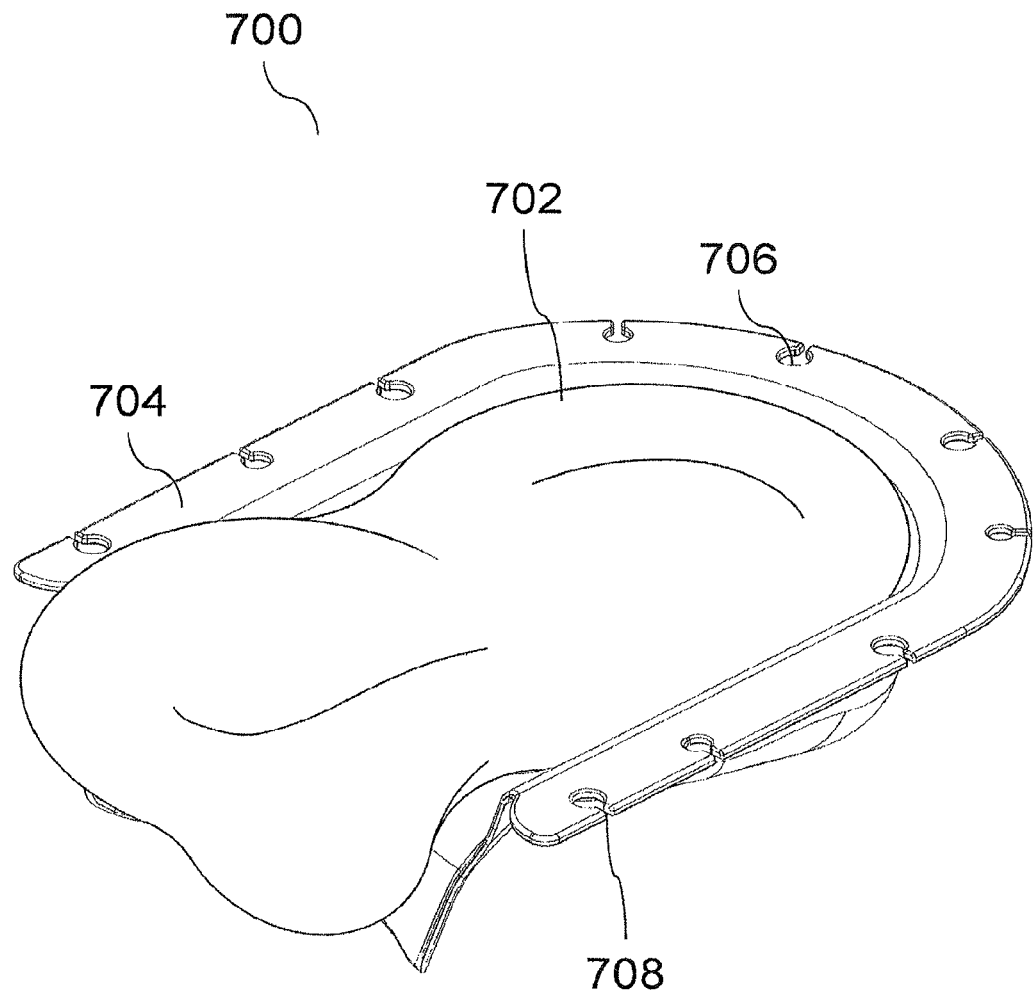
FIG. 19 is a diagram showing a cushion placed in a cushion holder according to aspects of the invention.
Figure 20:
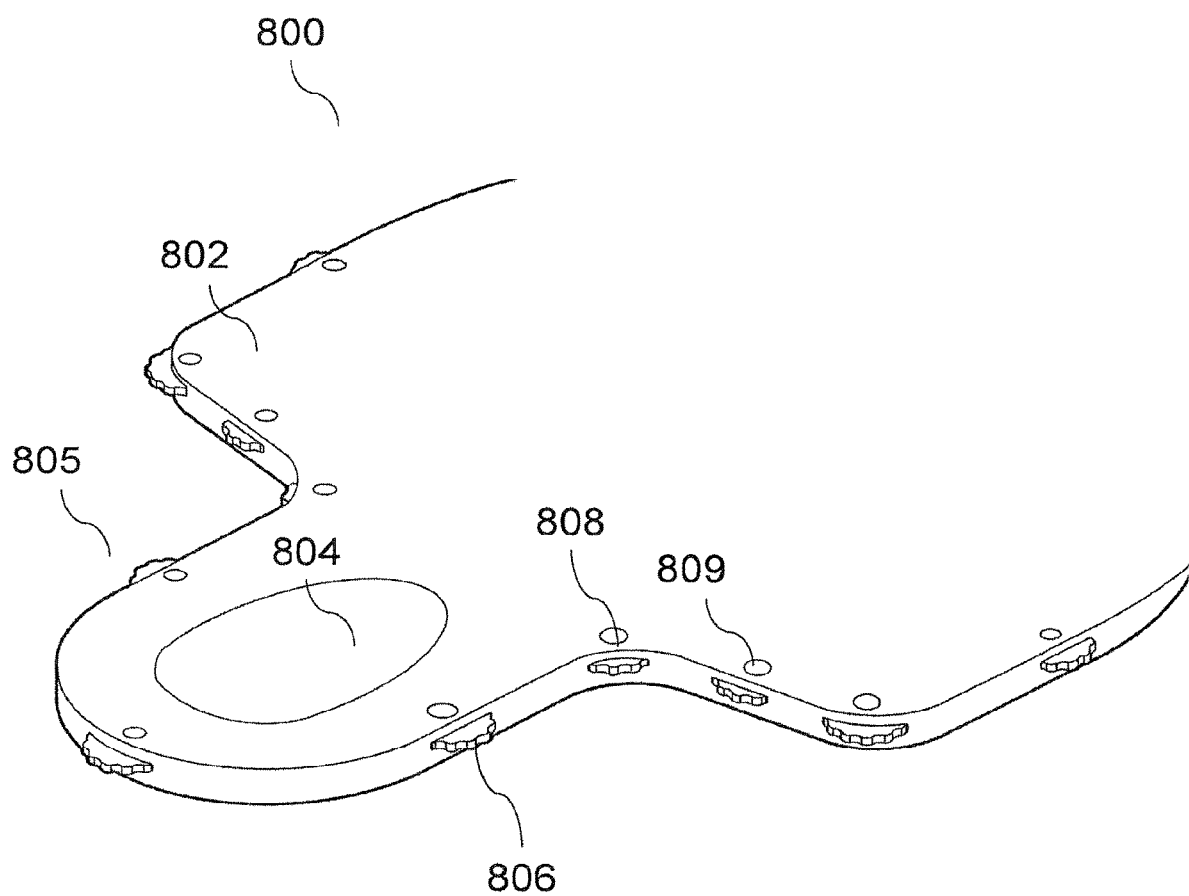
FIG. 20 depicts a patient immobilization device with adjustment mechanisms integrated into a support in accordance with aspects of the invention.
Figure 21:
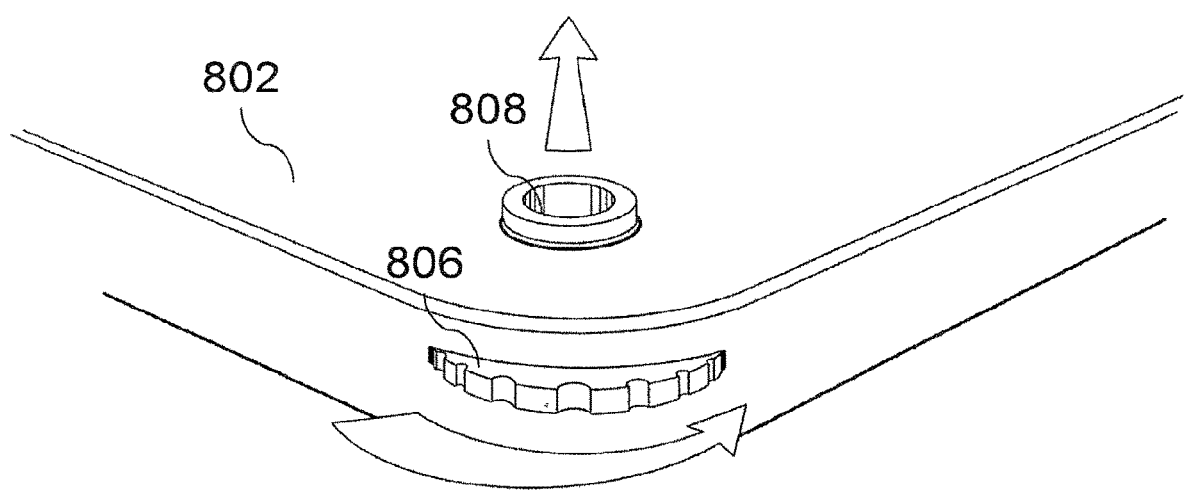
FIG. 21 depicts an adjuster mechanism for adjusting a distance between a support and an immobilization element in accordance with aspects of the invention.

In order for the formable cushion to be capable of repeatably and reliably retaining the patient's anatomy (e.g. the patient's head) in a stable, immobile position, cushion retaining device 230 is configured to support the formable cushion. In an exemplary embodiment, cushion retaining device 230 supports the formable cushion on the posterior surface of the cushion. As shown in FIG. 19, where formable cushion is shaped to cushion a patient's head, cushion retaining device 230 is contoured to support the posterior surface of the cushion, as well as the sides of the cushion around the top and sides of the user's head. This support assists in reliably and repeatably immobilizing the user's head during repeated medical procedures.

Cushion retaining device 230 is desirably formed from a rigid material to prevent deformation or movement of the formable cushion. Suitable materials for cushion retaining device 230 include, by way of example, fiber reinforced composites or plastics. Like the other components of apparatus 100, cushion retaining device 230 is preferably constructed from materials that are compatible with the procedure to be performed on the patient. Cushion retaining device 230 preferably has a thickness of no more than 2 mm.

As shown in FIG. 11A, cushion retaining device 230 is desirably indexed to support structure 190, so that the position of cushion retaining device 230 relative to support structure 190 can be tracked and repeated. To make repeated immobilization of the patient possible, the preform of apparatus 100 (not shown in FIG. 11A) may also be indexed to support structure 190, so that the elements on both sides of the patient's head are tracked with respect to an immobile object (i.e. support structure 190).

This cushion retaining device supports the cushion. The cushion retaining device is preferably contoured to provide a comfortable position for the patient. The cushion retaining device is preferably constructed of a stiff material to provide the maximum amount of support to the cushion. Examples of materials to be used include fiber reinforced composites, or any other material suitable for the application. The cushion retaining device is preferably thin to minimize its effect on the treatment beam. A preferred thickness is approximately 2 mm. This retaining device may be constructed of MR compatible materials to allow the device to be used for MR imaging.

In one embodiment the cushion retaining device is indexed to the same support structure as the anterior thermoplastic immobilization device as shown in FIG. 11A. This may be the surface that the patient is lying on or may be a secondary support structure. By indexing both immobilization devices to the same surface increased repeatability of positioning is achieved. This indexing may be accomplished by the locking pins or may be accomplished through another feature including but not limited to: pins, bosses, and recesses.

Figure 12:
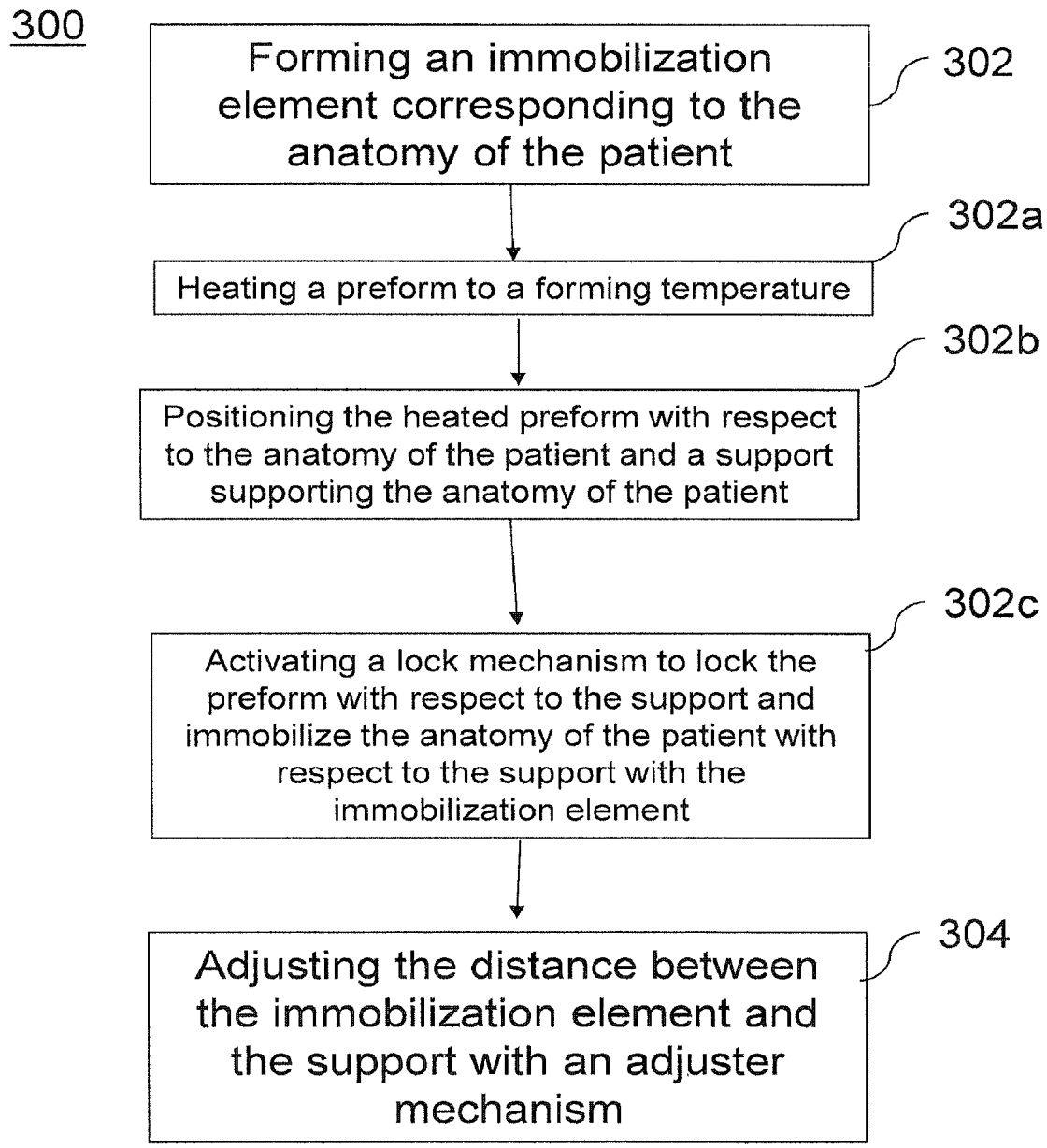
FIG. 12 is a flowchart illustrating the steps of an exemplary method for immobilizing a patient in accordance with aspects of the invention.

FIG. 12 is a flowchart illustrating an exemplary method 300 for immobilizing a patient in accordance with an aspect of the present invention. The steps of the method 300 of immobilizing an anatomy of a patient for treatment, including step 302 of forming an immobilization element corresponding to the anatomy of the patient. The forming step 302 includes step 302a of heating a preform to a forming temperature, step 302b of positioning the heated preform with respect to the anatomy of the patient and a support supporting the anatomy of the patient, and step 302c of activating a lock mechanism to lock the preform with respect to the support and immobilize the anatomy of the patient with respect to the support with the immobilization element. The method 300 also includes step 304 of adjusting, while the anatomy of the patient is in place in the immobilization element, a distance between the immobilization element and the support by selectively adjusting at least one adjuster mechanism coupled to at least one of the preform, the support, and the immobilization element.

In step 302, an immobilization element is formed over an anatomy of a patient. The immobilization element may be a preform formed of low melting temperature thermoplastic. At step 302a, the immobilization element may be formed by heating a preform to a forming temperature. This allows the immobilization element to be formed and contour to the anatomy of the patient.

In sub step 302b, the heated preform is positioned with respect to the anatomy of the patient. In one embodiment, the heated preform may be associated with a frame to create the immobilization device. The frame may be similar to the frames described above. In an embodiment, the frame may be positioned over a support, such that the support includes corresponding indexes to permit positioning of the frame. In another embodiment, the frame is positioned with another frame. For example, a second frame may include a support constructed of low temperature thermoplastic that supports an anatomy of a patient, and positioning the first frame over the second frame constructs a splint with the support and the immobilization element. The frame may also be positioned with itself in embodiments where the top of the frame is constructed to meet corresponding indexes on the bottom of the frame. For example, the immobilization element may be configured to wrap around the anatomy of the patient until one side of the frame meets with another side of the frame, as shown for example in FIG. 18.

In step 302c, a lock mechanism is activated to lock the preform to a support. The lock mechanism may be the locks such as those described above. The lock mechanism may be an interference lock configured to create an interference between the lock and the frame and/or support when the lock mechanism is activated. Locking the preform allows the preform to form into an immobilization element when the preform cools to room temperature.

In step 304, the distance between the immobilization element and the support is adjusted with an adjuster mechanism. The adjuster mechanism may be similar to the adjuster and adjustment mechanism as described above. The distance between the immobilization element and the support is adjusted to ensure a tight and accurate fit between the immobilization element, support, and anatomy of the patient. Advantageously, the adjusters disclosed herein permit adjustment of the distance between the immobilization and the support while the anatomy of the patient is immobilized and without removing the anatomy from the immobilization element, the immobilization element from the support, etc. Additionally, the distance between the immobilization element and the support may be adjusted without locking the immobilization element to the support (e.g., in an unlocked position). This allows for highly accurate, easily repeatable immobilization without the use of cumbersome parts and without interrupting the immobilization of the anatomy of the patient.

Method 300 is not limited to the above steps, but may include additional or alternative steps as would be understood by one of ordinary skill in the art from the description herein.

For one example, method 300 may include steps of treating the patient after the distance between the frame and the support are adjusted with the adjuster mechanism. The treatment may include stereotactic radiosurgery, radiosurgery, radiation treatment, cancer treatment, etc. The above list of treatments is exemplary and not exclusive. Those of skill in the art will understand various treatments that will benefit from and can utilize the disclosed systems, apparatus, and methods herein.

Referring back to FIGS. 1A and 1B, the preform 10 is formed over the head 11 of the patient 12. The frame 13 is split into two sides, and each side is provided with locking mechanisms 14 such as those described above. In such embodiments, the preform 10 is formed such that a portion 15 of the head 11 of the patient 12 is left open. These applications may be advantageously utilized in neurosurgery applications. Typical neurosurgery requires the head of the patient to be immobilized, and usual immobilization is performed by inserting screws or other fastening devices directly into the head of the patient. The preform 10 depicted in FIGS. 1A and 1B permits immobilization of the patient head while providing access to the patient's head to a neurosurgeon. Thus, the patient 12 can be immobilized non-evasively.

Figure 1C:
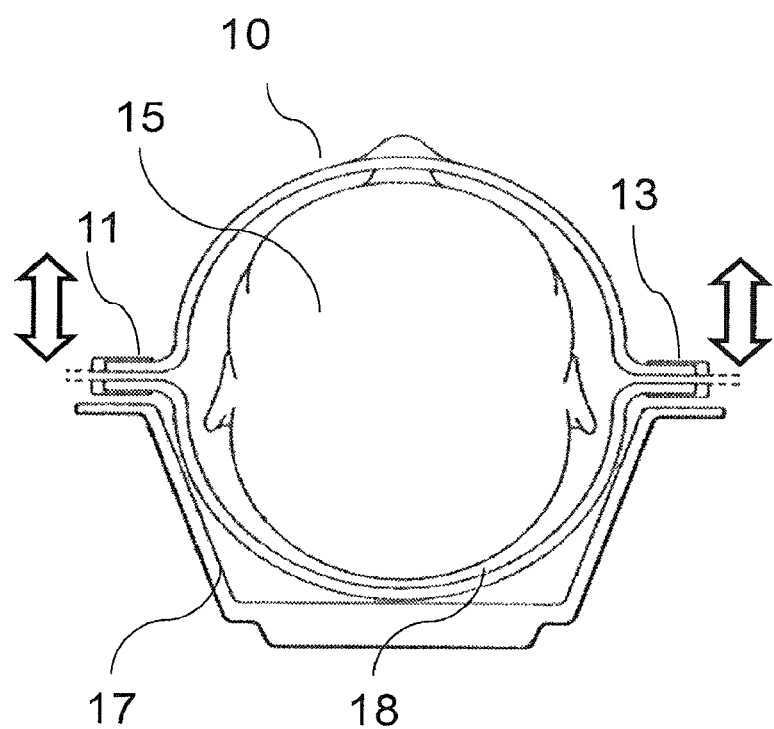
FIG. 1C is a diagram illustrating the adjustment between an anterior frame and a posterior support. A posterior element is also interposed between the frame and support in accordance with aspects of the invention.

In FIG. 1A, the head 15 of the patient rests in a cushion 16 that is placed in a support structure 17. In FIG. 1B, the head 15 of the patient 12 rests on a posterior preform 18 that is connected to the support 17. The posterior preform 18 may be constructed of a low melting temperature thermoplastic and formed to conform to the back of the head 15 of the patient 12. FIG. 1C depicts the adjustment of the distance between the frame 11 and 13 and the support 17. In FIG. 1C, the head 15 of the patient is shown resting on a posterior preform 18, although the head 15 may be resting on a cushion 16 as shown in FIG. 1A or both a cushion 16 and posterior preform 18. Adjustment of the adjuster mechanisms can selectively decrease the distance between the frames and support as indicated by the arrows, and selectively increase the distance between the frames and the support.

Referring to FIG. 2 again, a splint 20 is depicted. The splint 20 includes a support 23 and an immobilization element 22 that are formed over the arm 21 of a patient. The support 23 and immobilization element 22 may be rigid and/or constructed of a formable thermoplastic such that the support 23 and immobilization element 22 are contoured to the anatomy of the patient. As depicted, the immobilization element 22 includes a frame 24 that has co-located lock and adjuster mechanisms 26 integrated into the frame 24. The support 23 also includes a frame 25 that is adapted to attach to the frame 24 via the mechanisms 26. Alternatively, the mechanisms 26 may be positioned on the frame 25 of the support 23 or a combination of mechanisms 26 may be positioned on both the frame 24 of the immobilization element 22 and the frame 25 of the support 23.

Figure 13:
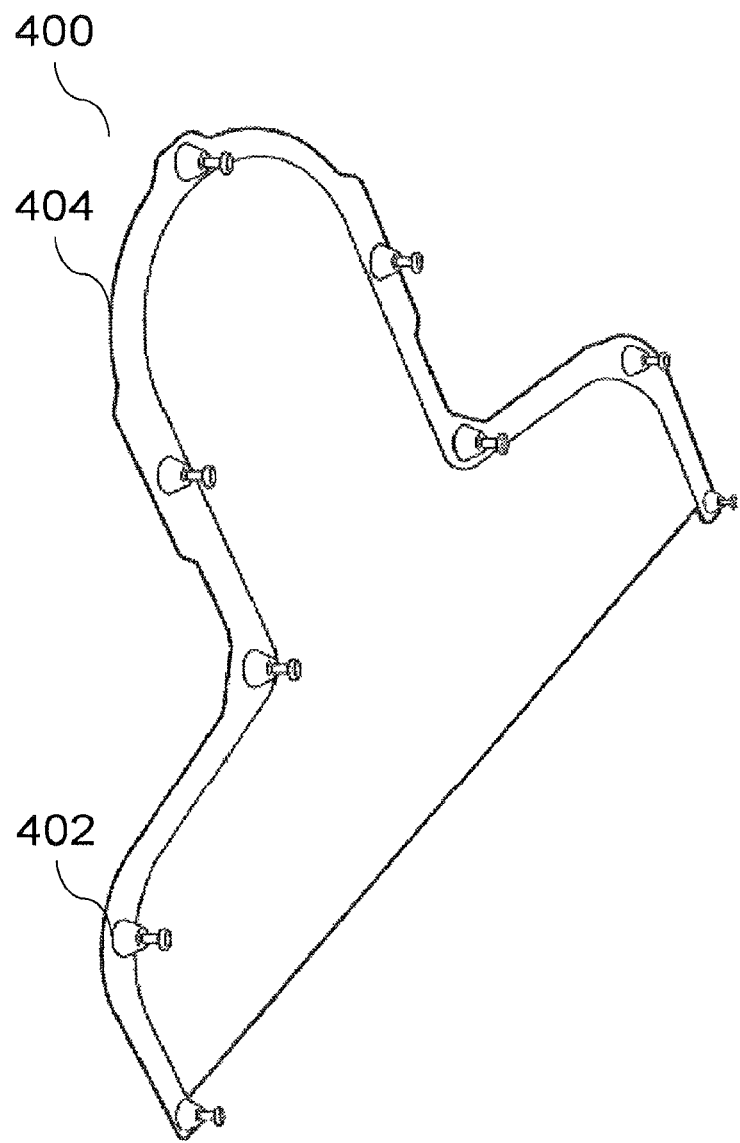
FIG. 13 is a diagram of an immobilization device in accordance with aspects of the invention.

With reference to FIG. 13, a patient immobilization device 400 is shown. The immobilization device 400 may be constructed of materials similar to the immobilization devices (e.g., preforms) as described above. The patient immobilization device 400 is adapted to be positioned and formed over the head, shoulders, and chest of a patient. Advantageously, the immobilization device 400, by being positioned over the chest and shoulders of the patient, can be used to immobilize the shoulders and chest of the patient for particular treatments, such as lymph node cancer treatment. The immobilization device 400 may reduce the movement of the tumor during treatment of the patient. The immobilization device 400 additionally includes locking mechanisms (depicted as co-located lock and adjuster mechanisms 402) positioned along the frame 404 of the immobilization device 400.

In the embodiments that utilize multiple lock and adjuster mechanisms, such as the embodiment illustrated in FIG. 13, the lock and adjuster mechanisms can be operated independently to lock, unlock, or adjust portions of the immobilization device as needed. For example, it is possible to use one or more selected adjuster mechanisms to tighten or loosen the fit of the immobilization device with respect to various portions of the patient's anatomy. This permits localized adjustment of the immobilization device. The adjuster mechanism can be configured to adjust the distance between a frame and a support at a location at which the adjuster mechanism is coupled to the frame, without decoupling the frame from the support and while the frame is in place on the support. For example, in an application in which the head of a patient is immobilized for treatment, it may be advantageous to adjust the fit of the immobilization device with respect to the patient's chin, forehead, or other portion of the patient's head without adjusting other portions of the patient's head.

Referring to FIG. 14, in addition to the thermoplastic mask 500 described above which is placed on the anterior side of the patient, an additional thermoplastic preform 502 may be used and formed to the posterior side of the patient's anatomy. By providing these two thermoplastic immobilization devices the patient is constrained on all sides of their head. This may provide superior immobilization as compared to using only a single thermoplastic immobilization device. In this embodiment when the locking mechanisms of the anterior immobilization device are moved to their second configuration (engaging mating holes on the support) they fix both the anterior and posterior immobilization devices in place. When the adjuster mechanism is rotated (or adjusted in embodiments where the adjuster is adjusted by other methods) it increases or decreases the distance between the frame of the anterior and posterior immobilization devices.

Figure 15:
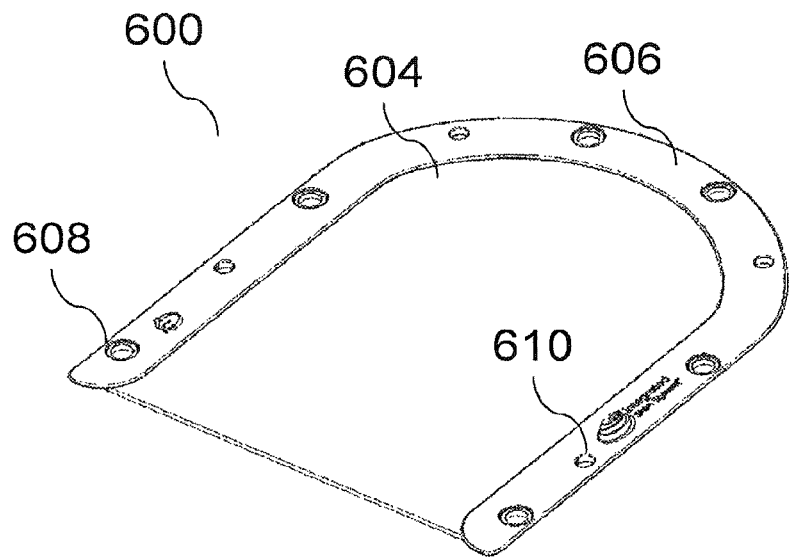
FIG. 15 is a diagram of a posterior mask according to aspects of the invention.
Figure 16:
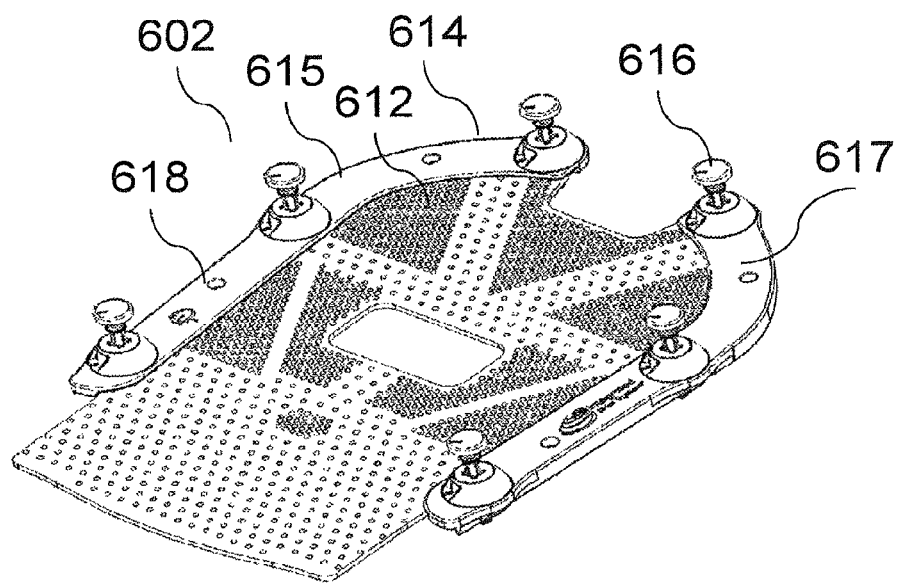
FIG. 16 is a diagram of an anterior mask in accordance with aspects of the invention.

FIGS. 15 and 16 depict a posterior preform mask 600 and anterior preform mask 602 that may be used in conjunction with the structure depicted in FIG. 14 in their unformed states. In the embodiments depicted in FIGS. 15 and 16, co-located mechanism 616 are positioned on the frame 614 of the anterior mask 602. The posterior preform 600 includes a thermoplastic mask 604, a frame 606, openings 608 and channels 610. The anterior preform 602 includes a perforated thermoplastic mask 612 (although the mask 612 may not be perforated), a frame 614 that includes a left section 615 and a right section 617, a series of co-located mechanisms 616 and channels 618. The openings 608 on the posterior preform 600 are configured to lock with the locking mechanisms 616 of the anterior preform 602. The channels 610 and 618 are configured to receive securing pins (not shown) from a support structure to align and secure the preforms to the structure.

Figure 17:
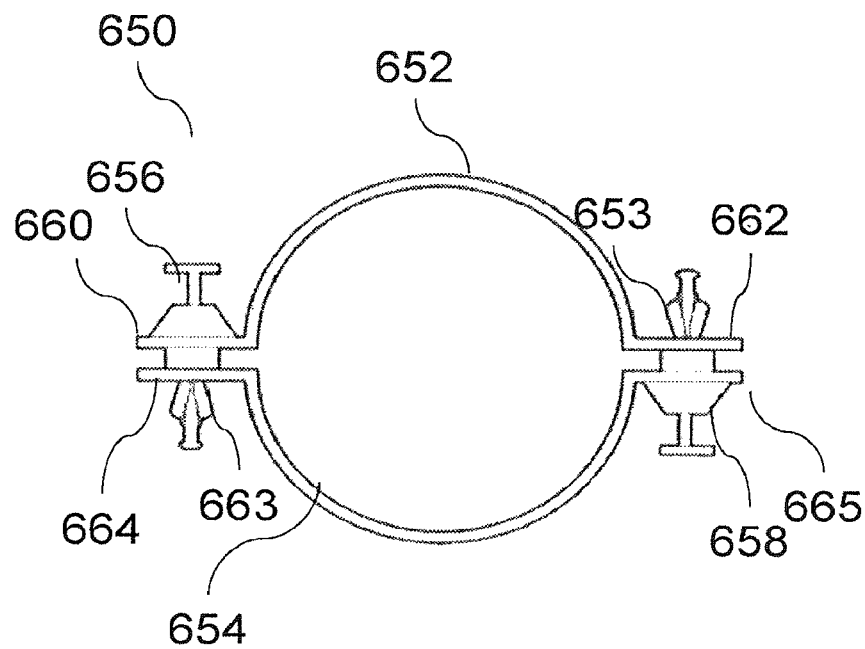
FIG. 17 is a diagram of an immobilization element incorporating both the frame and support in a symmetric fashion such that two similar or identical elements may be interlocked and adjusted with respect to each other according to aspects of the invention.
Figure 18:
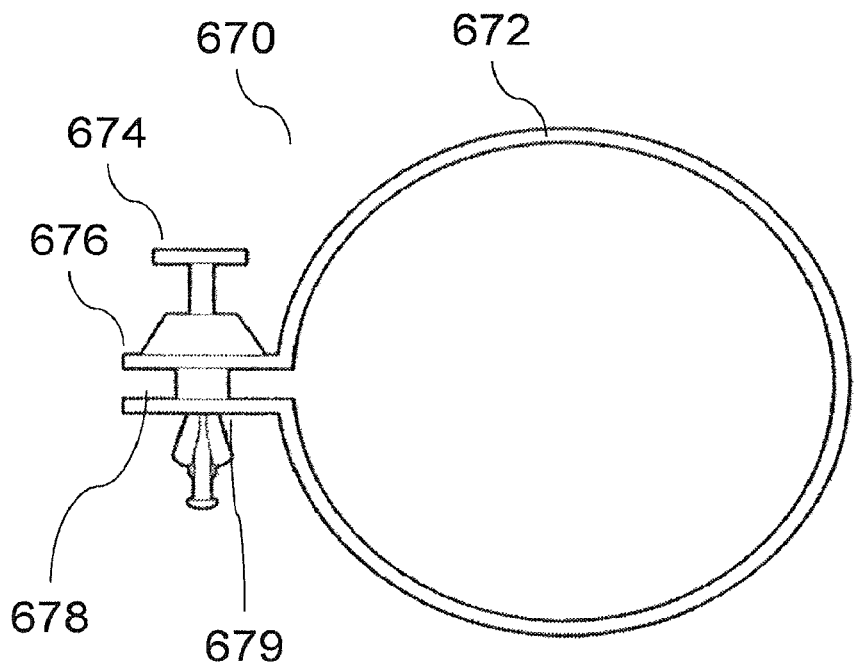
FIG. 18 is a diagram of a support or immobilization element in accordance with aspects of the invention. A frame and support are coupled to a low melting temperature thermoplastic such that the preform can be molded, interlocked to itself, and adjusted.

FIGS. 17 and 18 depict examples of immobilization systems 650 and 670. The system 650 includes a support 654 for supporting an anatomy of a patient, and an immobilization element 652. The immobilization element 652 has a first side frame 660 with a locking and adjusting mechanism 656 and a second side frame 662 with an opening 653. The support 654 includes a first side frame 664 with an opening 663 and a second side frame 665 with a locking and adjusting mechanism 658. The opening 663 is configured to receive the mechanism 656 and the opening 653 is configured to receive the mechanism 658 such that the mechanisms 656 and 658 are of opposite vertical arrangement. It is to be understood that the symmetry of this system allows either item 652 or item 654 to be considered the immobilization element and the other to be the support.

The system 670 includes an immobilization element 672 (e.g., a preform, a support, etc.), a locking and adjusting mechanism 674, a top frame 676 and a bottom frame 678. The immobilization element 672 may be formed to an anatomy of a patient such that the top frame 676 meets with the bottom frame 678, thereby aligning the locking and adjusting mechanism 674 with an opening 679 on the bottom frame 678. Thus, a single locking and adjusting mechanism (or a series of locking and adjusting mechanisms aligned on one side) may be utilized to lock the immobilization element 672 to itself and adjust the distance between the top frame 676 and bottom frame 678.

It is another object of this invention to provide an alternative to this second thermoplastic immobilization device located posterior to the patient. In another embodiment a formable patient cushion is used to immobilize the back of the patient's head.

FIG. 19 depicts another immobilization device in accordance with aspects of the invention. The device 700 includes a frame 704, and a formable cushion 702 within the device 700. The frame 704 of the device 700 includes a plurality of openings 706 that are configured to receive locking mechanisms and adjustable shims such as those described above. The plurality of openings 706 include a slit 708 that opens through the outside of the frame 704 to aid in manufacture.

FIGS. 20-23 depict another system with a lock mechanism and adjuster mechanism that permits adjustment of an immobilization device while immobilizing a patient according to aspects of the invention. The immobilization device 800 includes a support 802 that is capable of supporting the head of the patient (at the head portion 804) and shoulders of the patient. Positioned along the outer perimeter of the support 802 are a plurality of adjuster mechanisms 805 that are integrated into the support 802. The adjusters 805 take the form of a wheel 806 accessible from the outer perimeter of the support 802 and channels 808 within holes 809 formed in the support 802.

Figure 22A:
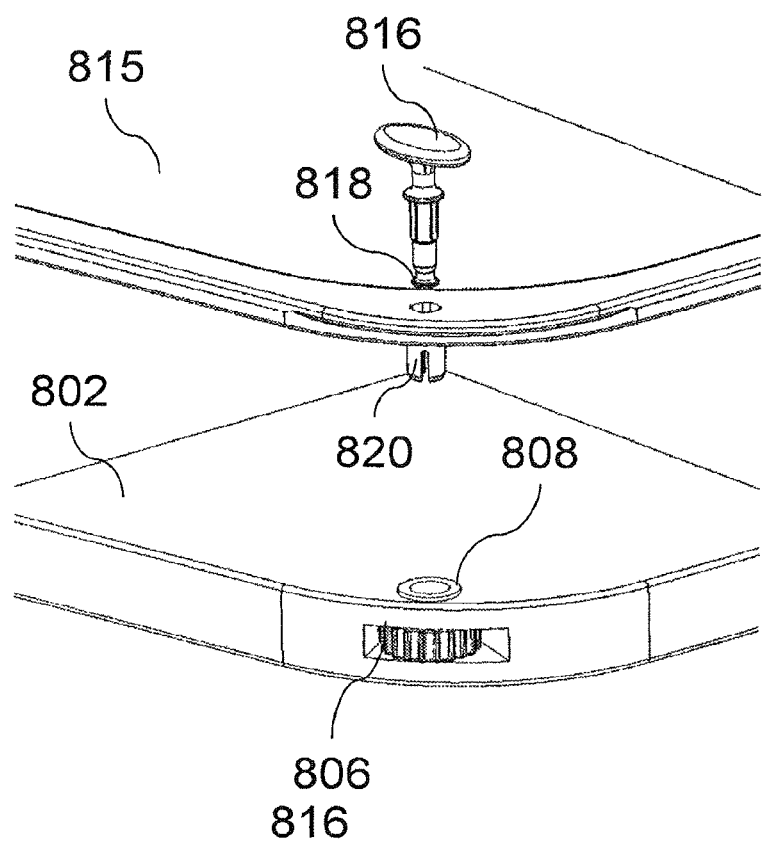
Figure 22B:
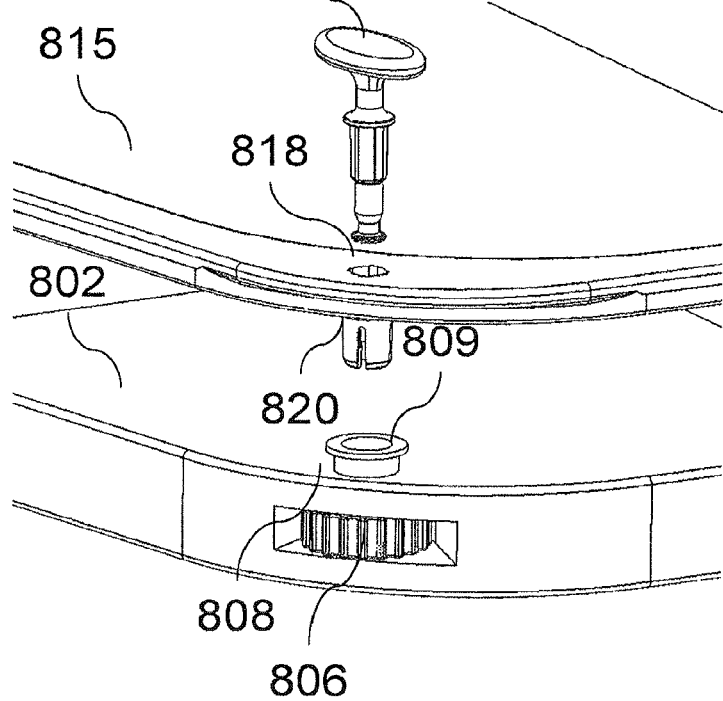

The wheels 806 may be rotated to adjust the distance between an immobilization device (such as a frame and preform) (and thereby a patient immobilization device, such as a frame with a preform) with respect to the support 802. As shown in FIGS. 22A, 22B, and 22C, the channel 808 is adapted to receive a lock mechanism 816. As depicted, the immobilization element 815 is positioned above the support 802, and includes extensions 820 formed on the underside of the element 815. The immobilization element 815 includes openings 818 through which a lock mechanism 816 may be inserted. The channel 808 includes a hole 809 that is adapted to receive the extensions 820 and the lock mechanism 816. The outer perimeter of the channel 808 has formed on it a thread 824, although the channel 808 may also or in the alternative have formed on it a cam surface to facilitation rotation and vertical displacement of the channel.

The hole 809 of the channel has an upper portion 828 and a lower portion 826 of larger diameter, and the upper portion 828 and lower portion 826 are separated by an edge 830. The extensions 820 are inserted into the hole 809 such that they extend past the edge 830 and into the lower portion 826. When the lock mechanism 816 is inserted into the hole 809 and through the middle of the extensions 820, the diameter of the lock mechanism 816 causes the extensions 820 to push radially outward, such that they bear against the inner wall of the hole 809 and the edge 830. By extending radially outward, the extensions 820 form an interference lock between the immobilization element 815 and the support 802.

When locked (and also when unlocked), the upper surface 811 of the channel 808 bears against the lower surface of the immobilization element 815. The distance between the immobilization element 815 and the support 802 may be adjusted by the adjuster mechanism provided by the wheel 806. Referring to FIG. 23, the wheel 806 includes a matching formation along the center to match the threading or cam surface 824 of the channel 808. A cam surface with a bearing surface may be configured to increase the distance between the immobilization element and the support upon relative movement of the cam surface with respect to the immobilization element or the support. The rotation of the wheel 806 moves the channel 808 vertically. The top surface 811 of the channel 808 that is engaged with the lower surface of the immobilization device 815 such that movement of the wheel 806 adjusts the vertical position of the channel 808, thereby adjusting the distance between the surface 802 and the immobilization element 815, The wheel 806 may also include indicators (e.g., numbers) on the surface to indicate to the user of the system as to the vertical position of the channel 808, and may also include indexing mechanisms such as those described above. Advantageously, the adjustment of the distance between the support 802 and the immobilization element 815 may be performed while the anatomy of a patient is immobilized and while the immobilization element 815 is still attached to the support 802.

The embodiments depicted in FIGS. 22A-22C may advantageously permit adjustment of the distance between the immobilization device and the support while the immobilization device and the support are unlocked or locked with respect to one another, in contrast to one embodiment described previously with reference to FIG. 4D. By providing adjustment while the support and immobilization are optionally locked or unlocked, the amount of time required to adjust the system to the desired level can be reduced because the time necessary to unlock and relock is eliminated.

Figure 24A:
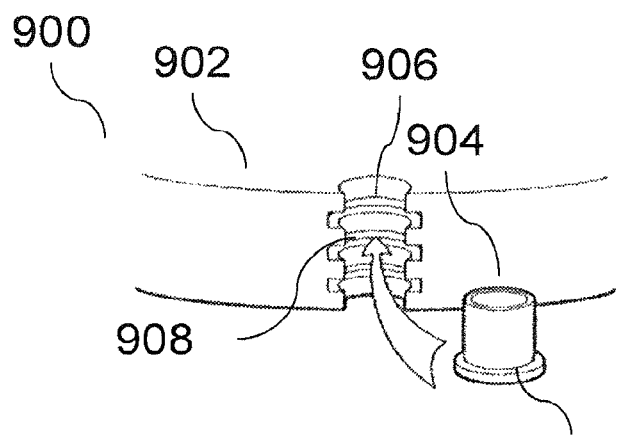
FIGS. 24A, 24B, and 24C are diagrams of an adjustment mechanism according to aspects of the invention.
Figure 24B:
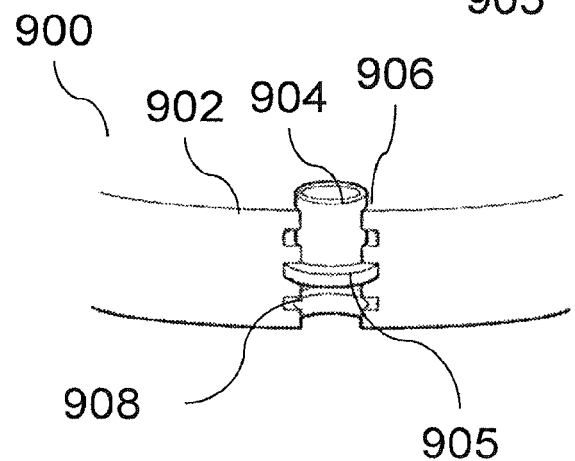
Figure 24C:
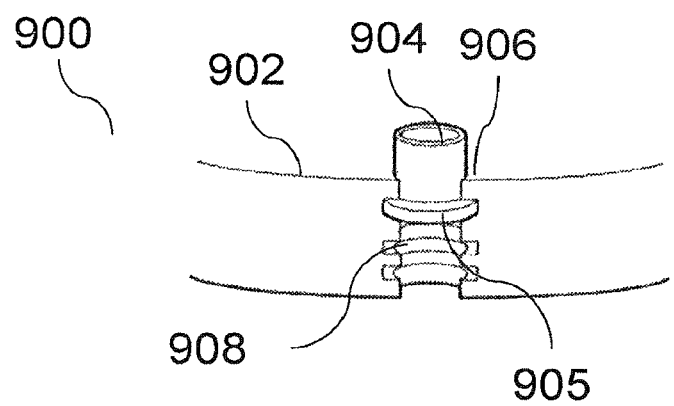

Alternative adjustment mechanisms may be utilized in accordance with aspects of the invention. An example of such a system is depicted in FIGS. 24A-24C. The system 900 includes a support 902, a channel 904 with a bottom portion 905 of larger diameter, and a notched column 906 formed in the support 902. The notches 908 are adapted to receive the bottom portion 905 of the channel 904, such that the vertical position of the channel 904 with respect to the surface 902 may be selectively adjusted by insertion of the bottom portion 905 into differently positioned notches 908 in the notched column 906.

Figure 25A:
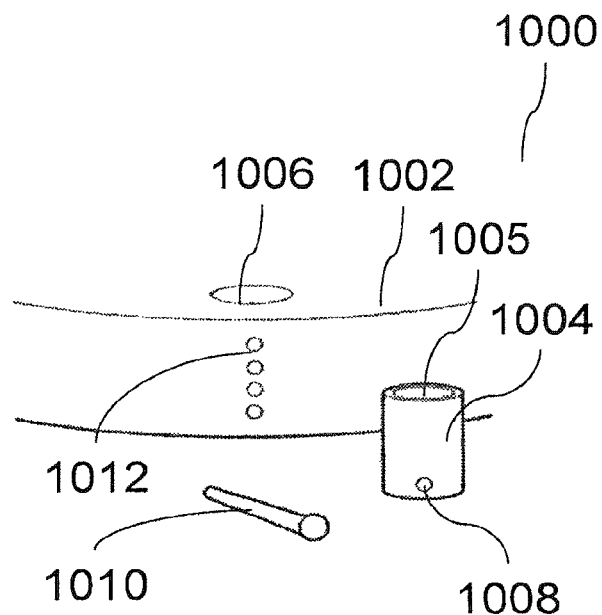
FIGS. 25A and 25B are diagrams of an adjustment mechanism in accordance with aspects of the invention.
Figure 25B:
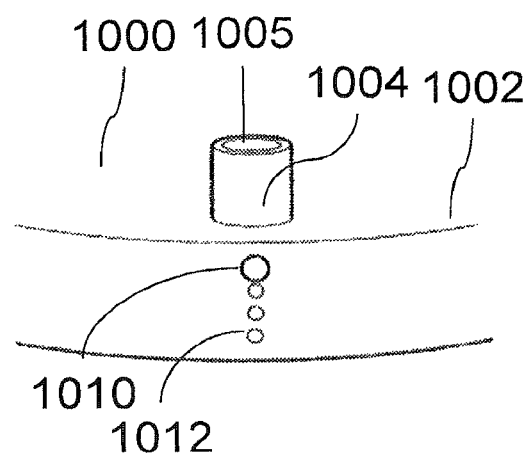

FIGS. 25A and 25B depict another example of an adjuster mechanism according to aspects of the invention. The system 1000 includes a support 1002, a channel 1004 with an opening 1005 and peg hole 1008. An opening 1006 is formed in the support 1002 and corresponding peg holes 1012 are formed on the outer perimeter of the support 1000 at the location of the opening 1006. The position of the channel 1004 may be adjusted by insertion of a peg 1010 into the peg hole 1008 through a peg hole 1012 formed on the outer perimeter of the support 1002.

In an additional embodiment, the lock mechanism and/or the adjuster mechanism can be coupled directly to the preform. For example, the lock mechanism or adjuster mechanism may be pre-assembled to the preform, or assembled at the time of forming the preform to an anatomy of a patient.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. An apparatus for immobilizing an anatomy of a patient, the apparatus comprising:
    a preform formed from a low melting temperature thermoplastic, the preform being configured to be formed to the anatomy of the patient;
    a frame coupled to the preform and adapted to be coupled to a support configured to support the anatomy of the patient;
    a lock mechanism coupled to the frame and configured to lock the frame to the support; and
    an adjuster mechanism coupled to the frame and configured to selectively adjust a distance between the frame and the support while the frame is coupled to the support;
    the lock mechanism comprising a plunger coupled to the frame and movable relative to the frame;
    the lock mechanism further comprising a shaft coupled to the frame and defining a through hole for accommodating the plunger, the shaft having a surface positioned to bear against the support; and
    the adjuster mechanism being configured to move the shaft relative to the frame, thereby adjusting the spacing of the frame relative to the support by contact between the surface of the shaft bearing against the support.

2. The apparatus of claim 1, the lock mechanism having an unlocked state and a locked state configured to lock the frame to the support, the lock mechanism being attached to the frame in the unlocked state and in the locked state.

3. The apparatus of claim 2, the lock mechanism having a surface positioned to resist separation of the frame from the support when the lock mechanism is in the locked state.

4. The apparatus of claim 3, the lock mechanism having at least one extension positioned to create an interference lock when the lock mechanism is in the locked state, the at least one extension providing the surface positioned to resist the separation of the frame from the support.

5. The apparatus of claim 2, the adjuster mechanism being attached to the frame when the lock mechanism is in the unlocked state and in the locked state.

6. The apparatus of claim 1, wherein the distance between the frame and the support is adjustable while the frame is in place on the support and the frame is not removed or separated from the support.

7. The apparatus of claim 6, wherein the distance between the frame and the support is adjustable while the frame and the support are in a locked arrangement.

8. The apparatus of claim 6, wherein the distance between the frame and the support is adjustable while the frame and the support are in a partially locked arrangement.

9. The apparatus of claim 6, wherein the distance between the frame and the support is adjustable while the frame and the support are in an unlocked arrangement.

10. The apparatus of claim 1, wherein the frame includes frame portions, the lock mechanism comprising plural locks with at least one lock attached to each of the frame portions.

11. The apparatus of claim 10, the adjuster mechanism comprising plural adjusters with at least one adjuster attached to each of the frame portions.

12. The apparatus of claim 11, wherein at least two of the plural adjusters are attached to each of the frame portions.

13. The apparatus of claim 1, the adjuster mechanism having a surface positioned for movement relative to the frame to selectively adjust the distance between the frame and the support.

14. The apparatus of claim 13, the surface of the adjuster mechanism being a ramped surface positioned for movement relative to the support and to selectively adjust the distance between the frame and the support while the frame is coupled to the support.

15. The apparatus of claim 1, wherein the lock mechanism and the adjuster mechanism are co-located with respect to one another.

16. The apparatus of claim 1, wherein the adjuster mechanism adjusts the distance between the frame and the support in discrete distance increments.

17. The apparatus of claim 1, wherein the adjuster mechanism does not need to be decoupled from the frame or the support to adjust the distance extending between the frame and the support, the adjuster mechanism being configured to adjust the distance between the frame and the support at a location at which the adjuster mechanism is coupled to the frame, without decoupling the frame from the support and while the frame is in place on the support.

18. The apparatus of claim 1, wherein the adjuster mechanism comprises an indicator that provides visual indication of the distance maintained between the frame and the support at a location at which the adjuster mechanism is coupled to the frame.

19. The apparatus of claim 1, wherein the adjuster mechanism comprises a rotatable adjuster.

20. The apparatus of claim 1, wherein the lock mechanism comprises a releasable lock.

21. The apparatus of claim 1, the lock mechanism comprising an interference lock configured to create interference between the interference lock and at least one of the frame and the support.

22. The apparatus of claim 1, the lock mechanism comprising plural locks operable independently of one another to lock portions of the frame to the support.

23. The apparatus of claim 1, the adjuster mechanism comprising plural adjusters operable independently of one another to adjust the distance between the support and portions of the frame.

24. The apparatus of claim 1, further comprising an indicator positioned to provide a visual indication of the distance between the frame and the support at a location at which the adjuster mechanism is coupled to the frame.

25. The apparatus of claim 1, wherein the frame is attached to the preform and is adapted to be releasably locked to the support;
   the lock mechanism having an unlocked state and a locked state configured to releasably lock the frame to the support, wherein the lock mechanism is attached to the frame in the unlocked state and in the locked state; and
   the adjuster mechanism is capable of selectively adjusting the distance between the frame and the support without decoupling the frame from the support and while the frame is in place on the support.

26. An apparatus for immobilizing an anatomy of a patient, the apparatus comprising:
   a preform formed from a low melting temperature thermoplastic, the preform being configured to be formed to the anatomy of the patient;
   a frame coupled to the preform and adapted to be coupled to a support configured to support the anatomy of the patient;
   a lock mechanism coupled to the frame and configured to lock the frame to the support; and
   an adjuster mechanism coupled to the frame and configured to selectively adjust a distance between the frame and the support while the frame is coupled to the support;
   the lock mechanism being attached to the frame in an unlocked state and in a locked state, the lock mechanism having a plunger coupled for movement relative to the frame and having an unlocked state and a locked state configured to lock the frame to the support, the lock mechanism having at least one extension positioned to create an interference lock when the plunger is in the locked state; and
   the adjuster mechanism being co-located with the lock mechanism and comprising a shaft coupled to the frame and defining a through hole for accommodating the plunger, the shaft having a surface positioned to bear against the support, the plunger and the shaft being coupled such that the plunger and the shaft rotate together relative to the frame, the shaft being movable relative to the frame to adjust the spacing of the frame relative to the support by contact between the surface of the shaft bearing against the support.

27. The apparatus of claim 26, the lock mechanism and the adjuster mechanism being provided by a co-located lock and adjuster, wherein the co-located lock and adjuster includes a casing configured to attach the co-located lock and adjuster directly to the frame, the casing including a through-hole for accommodating the shaft and the plunger.

* * * * *